US012629384B2

(12) United States Patent
Mascal et al.

(10) Patent No.: US 12,629,384 B2
(45) Date of Patent: May 19, 2026

(54) USE OF 8,9-DIHYDROCANNABIDIOL COMPOUNDS

(71) Applicant: The Regents of the University of California, Oakland, CA (US)

(72) Inventors: Mark Mascal, Oakland, CA (US); Nikolay Shevchenko, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 1108 days.

(21) Appl. No.: 17/436,015

(22) PCT Filed: Mar. 9, 2020

(86) PCT No.: PCT/US2020/021670

§ 371 (c)(1),
(2) Date: Sep. 2, 2021

(87) PCT Pub. No.: WO2020/185661

PCT Pub. Date: Sep. 17, 2020

(65) Prior Publication Data

US 2022/0183998 A1 Jun. 16, 2022
US 2025/0152520 A2 May 15, 2025

Related U.S. Application Data

(60) Provisional application No. 62/815,735, filed on Mar. 8, 2019.

(51) Int. Cl.
*A61K 31/00* (2006.01)
*A61P 25/08* (2006.01)

(52) U.S. Cl.
CPC ............ *A61K 31/658* (2023.05); *A61P 25/08* (2018.01)

(58) Field of Classification Search
CPC ....... A61K 31/05; A61P 25/08; C07D 203/26; C07C 2601/16; C07C 39/15; C07C 39/23
See application file for complete search history.

(56) References Cited

U.S. PATENT DOCUMENTS

| | | | |
|---|---|---|---|
| 4,018,777 | A | 4/1977 | Zaugg |
| 2018/0338931 | A1 | 11/2018 | Guy et al. |

FOREIGN PATENT DOCUMENTS

| | | | |
|---|---|---|---|
| CN | 108785298 | 11/2018 | |
| CN | 109106699 | 1/2019 | |
| JP | 2013523708 | 6/2013 | |
| JP | 2017524672 | 8/2017 | |
| WO | 2011121351 | 10/2011 | |
| WO | WO-2012011112 A1 * | 1/2012 | ............. C07C 62/32 |

(Continued)

OTHER PUBLICATIONS

Yuichi Kobayashi. Akira Takeuchi, Yong-Gang Wang, Synthesis of Cannabidiols viaAlkenylation of CyclohexenylMonoacetate, Org. Lett. 2006, 8, 13, 2699-2702 (Year: 2006).*

(Continued)

*Primary Examiner* — Clinton A Brooks
*Assistant Examiner* — Izabela Schmidt
(74) *Attorney, Agent, or Firm* — Norton Rose Fulbright US LLP

(57) ABSTRACT

The present invention provides a method of treating or mitigating seizures comprising compounds as described herein.

2 Claims, 2 Drawing Sheets

THC

CBD

H2CBD

(56) References Cited

FOREIGN PATENT DOCUMENTS

WO 2017008136 1/2017

OTHER PUBLICATIONS

Shimon Ben-Shabat et al., J. Med. Chem. 2006, 49, 1113-1117 (Year: 2006).*
B. Cardillo et al., Tetrahedron Letters No. 10, pp. 945-940, 1972 (Year: 1972).*
https://pubchem.ncbi.nlm.nih.gov/compound/67524115, record created Nov. 30, 2012 (Year: 2012).*
Yuichi Kobayashi. Akira Takeuchi, Yong-Gang Wang, Org. Lett. 2006, 8, 13, 2699-2702 (Year: 2006).*
R. Michoulam, Y. Shvo Tetrahedron, 19 (1963), p. 2073-2078 (Year: 1963).*
Ichino, Kazuhiko; Tanaka, Hitoshi; Ito, Kazuo, Tetrahedron (1988), 44(11), 3251-60 (Year: 1988).*
Pierre-Olivier Delaye, Pedro Lameiras, Nelly Kervarec, Catherine Mirand, and Hatice Berber the Journal of Organic Chemistry 2010 75 (8), 2501-2509. (Year: 2010).*
International Search Report and Written Opinion issued in corresponding PCT Application No. PCT/US2020/0216705, mailed Sep. 17, 2020.
Mascal, Mark et al., "Synthetic, non-intoxicating 8,9-dihydrocannabidiol for the mitigation of seizures", *Scientific Reports*, 9, 7778, 2019.
Morales, P. et al., "An Overview on Medicinal Chemistry of Synthetic and Natural Derivatives of Cannabidiol", *Frontiers in Pharmacology*, 8, Article 422, 1-18, 2017.
Pubchem CID 11338972, pp. 1-7, Create Date: Oct. 26, 2006; p. 2.
Pubchem CID 11645860, pp. 1-8, Create Date: Oct. 26, 2006; p. 2.
Pubchem CID 125456248, pp. 1-9, Create Date: Apr. 10, 2017; p. 2.
Pubchem CID 130436940, pp. 1-10, Create Date: Oct. 7, 2017; p. 2.
Pubchem CID 26346, pp. 1-15, Create Date: Jun. 24, 2005; p. 2.
Pubchem CID 53357350, pp. 1-11, Create Date: Sep. 19, 2011; p. 2.
Pubchem CID 53462477, pp. 1-7, Create Date: Oct. 30, 2011; p. 2.
Pubchem CID 59444389, pp. 1-10, Create Date: Aug. 20, 2012; page 2.
Pubchem CID 67524115, pp. 1-9, Create Date: Nov. 30, 2012; p. 2.
Pubchem CID 71053731, pp. 1-11, Create Date: Mar. 21, 2013; p. 2.
Pubchem CID 76382623, pp. 1-8, Create Date: Jul. 30, 2014; p. 2.
Tauriga Sciences, Inc. to Showcase TopiCanna Cream and Other Natural Wellness Products at Te2015 Southern California Cannabis Cup, PR Release, pp. 1-3, 2015.
Ben-Shabat, S. et al., "New Cannabidiol Derivatives: Synthesis, Binding to Cannabinoid Receptor, and Evaluation of Their Antiinflammatory Activity", *J. Med. Chem.*, 49: pp. 1113-1117, 2006.
Belikov et al. "Pharmaceutical chemistry: manual", *Moscow: MEDpress-inform*, ppl. 27-29, 2007.(English translation not available at this time).
Dyson et al. "Chemistry of Synthetic Drugs", English—Russian translation; *Moscow: Mir*, pp. 12-19, 1964.
Office Action issued in corresponding Chinese Application No. 2020800301869 dated Oct. 27, 2023. (English Translation).
Office Action issued in corresponding Russian Application No. 2021129239, dated Oct. 3, 2023. (English Translation).
Cardillo et al., "Alkylation of resorcinols with monoterpenoid allylic alcohols in aqueous acid: synthesis of new cannabinoid derivatives", *Tetrahedron letters*, No. 10, pp. 945-948, Mar. 1, 1972.
Carlini et al., "Anticonvulsant activity of four oxygenated cannabidiol derivatives", *Research communications in chemical pathology and pharmacology*, vol. 12, No. 1, pp. 1-15, Aug. 31, 1975.
Devinsky, et al. "Trial of Cannabidiol for Drug-resistant seizures in the Dravet syndrome", *The New England Journal of Medicine*, vol. 376, No. 21, pp. 2011-2020, May 25, 2017.
Extended European Search Report issued in corresponding European Application No. 20769683.2, dated Feb. 21, 2023.
Huizenga, et al., "Preclinical safety and efficacy of cannabidivarin for early life seizures", *Neuropharmacology*, vol. 148, pp. 189-198, 2019.
Ichino et al, "Two novel flavonoids from the leaves of lindera umbellate var. Lancea and L. Umbellata", Tetrahedron, vol. 44, No. 11, pp. 3251-3260, Jan. 1, 1988.
Nalli, et al., "Analyzing the role of cannabinoids as modulators of Wnt/[bets]-catenin signaling pathway for their use in the management of neuropathic pain", *Bioorganic & Medicinal Chemistry Letters*, vol. 29, No. 9, pp. 1043-1046, Mar. 11, 2019.
Usami et al, "Synthesis and pharmacological evaluation in mice of halogenated cannabidiol derivatives", *Chem. Pharm. Bull.* , vol. 47, No. 11, pp. 1641-1645,1999.

* cited by examiner

THC CBD H2CBD

USE OF 8,9-DIHYDROCANNABIDIOL COMPOUNDS

CROSS-REFERENCES TO RELATED APPLICATIONS

This application claims priority to International PCT Application No. PCT/US2020/021670, filed Mar. 9, 2020 which claims priority to U.S. Provisional Application No. 62/815,735, filed Mar. 8, 2019, the contents of which are incorporated herein by reference in their entirety for all purposes.

BACKGROUND

There can be a fine line between therapeutic intervention and substance abuse, and possibly nowhere is this better exemplified than with herbal cannabis and its products. Therapies involving cannabis have been the treatment of last resort for some cases of refractory epilepsy, and this has been among the strongest medical justifications for legalization of marijuana. In order to circumvent the hypnotic effects of 49-tetrahydrocannabinol (THC), some studies have concentrated on its less intoxicating isomer cannabidiol (CBD). However, CBD, like all natural cannabinoids, is a controlled substance in most countries, and its conversion into THC can be easily performed using common chemicals. Alternatives to CBD include 8,9-dihydrocannibidiol (H2CBD) and it's analogs. H2CBD is a fully synthetic analogue of CBD that is prepared from inexpensive, non-cannabis derived compounds. H2CBD was found to have effectiveness comparable to CBD both for decreasing the number and reducing the severity of pentylenetetrazole-induced seizures in rats. Finally, H2CBD cannot be converted by any reasonable synthetic route into THC, and so could be freely marketed without potential for abuse.

There is currently a great deal of research activity around the potential for phytocannabinoids, i.e. compounds that occur naturally in the hemp plant (*Cannabis* spp.). to treat a wide range of medical conditions, including anxiety, glaucoma, epilepsy, spasticity, inflammation, neurodegenerative diseases, affective disorders, and even cancer. The opportunities around the therapeutic potential of cannabinoids are however weighed against a range of drawbacks, including adverse health effects, potential for abuse, cognitive and motor impairment, psychiatric disturbances, legal issues, and the environmental impacts of marijuana cultivation. Beyond this, herbal cannabis has been shown to contain >500 chemical entities, including around 100 cannabinoids alongside a variety of other terpenes, phenolics, flavonoids, lipids, and steroids, the toxicity and mutagenic nature of which are largely unexplored. Of the two major cannabinoids that occur in cannabis, i.e. $\Delta^9$-tetrahydrocannabinol (THC) and cannabidiol (CBD), the deleterious effects (intoxication, ataxia, tachycardia, somnolence, dry mouth, and hyperphagia) are primarily attributed to the former, and for that reason CBD has often been singled out for pharmacological investigations.

CBD is derived by extraction from the cannabis plant. A range of impurities may be present, and there is a growing concern for contamination by pesticides, particularly in the current, largely unregulated climate. Even if pure CBD is marketed, the deliberate chemical conversion of CBD to THC is technically trivial. Were CBD to become freely available, it could lead to a culture similar to that of the pseudoephedrine to methamphetamine "meth lab" phenomenon, except that "hash labs" would involve a logistically far simpler chemical transformation. Pure THC, containing no CBD to antagonize its psychotropic effects, would be a potentially dangerous drug. A collateral liability of the derivation of CBD from cannabis is the cultivation of hemp, with potential environmental impacts in terms of heavy water usage and pesticide/herbicide effluent burden. Legalization of marijuana will inevitably also lead to private cultivation using methods not intended to manage potential environmental damage. Finally, the possible impact of legalized marijuana on healthcare systems, which in the US has been recently highlighted in the areas of accidental injuries, unintentional ingestion of cannabis edibles by children, and reproductive health, may be considerable.

Among the potential therapeutic indications of cannabis, it can be argued that its highest profile use is as an antiepileptic. Epilepsy is the general term given to a spectrum of conditions characterized by recurrent, unpredictable seizures, the consequences of which often have a profound effect on quality of life. Historical and anecdotal evidence, along with a number of case studies documenting the practically unique efficacy of cannabis to treat refractory cases of epilepsy, have led to strong advocacy in favor of the legalization of marijuana. Clinical data to support the therapeutic potential of CBD as an antiepileptic, while encouraging, are limited in terms of number of studies and subjects involved. On the other hand, preclinical evidence for anticonvulsant activity of CBD and THC in acute animal models of seizures is extensive.

One advantage of H2CBD is that, despite its similarity to CBD, it is not present in cannabis extracts and therefore not a controlled substance. Perhaps even more importantly, there is no reasonable synthetic route for the conversion of H2CBD to THC, in stark contrast to CBD itself, as H2CBD lacks the double bond which enables the conversion of CBD to THC. Although H2CBD has been prepared from natural CBD, H2CBD can also be prepared via an efficient, fully synthetic approach in order to avoid the intermediacy of any scheduled substance and thereby also circumvent any necessity for the cultivation of cannabis to supply H2CBD. What is needed are analogs of H2CBD and methods of using these compounds for treating seizures and other conditions. Surprisingly, the present invention meets this and other needs.

BRIEF SUMMARY OF THE INVENTION

In one embodiment, the present invention provides a method of treating or mitigating a seizure, comprising administering to a subject in need thereof, a therapeutically effective amount of a compound of Formula I:

(I)

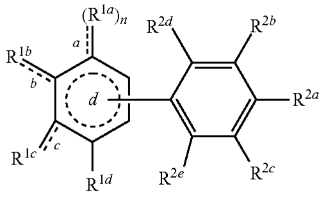

or a pharmaceutically acceptable salt thereof, without inducing hypnotic effects in the subject, thereby treating the seizure, wherein: n is 1 or 2; $R^{1a}$ and $R^{1d}$ are each independently —$CO_2R^{1c}$, $C_{1-20}$ alkyl, $C_{2-20}$ alkenyl or $C_{2-20}$ alkynyl, wherein at least one of $R^{1a}$ or $R^{1d}$ is methyl or isopropyl; $R^{1b}$ and $R^{1c}$ are each independently hydrogen or oxygen; alternatively, when $R^{1b}$ is oxygen, $R^{1b}$ is combined with $R^{1a}$ and the atoms to which they are attached to form an epoxide ring; alternatively, $R^{1b}$ is combined with $R^{1d}$ and the atoms to which they are attached to form a $C_{4-8}$ cycloalkyl, wherein the cycloalkyl is substituted with 1-3 $R^{1c}$ groups; $R^{1c}$ is H, $C_{1-20}$ alkyl, $C_{2-20}$ alkenyl or $C_{2-20}$ alkynyl; $R^{2a}$ is —$OR^{2f}$, $C_{1-20}$ alkyl, $C_{2-20}$ alkenyl or $C_{2-20}$ alkynyl; $R^{2b}$ and $R^{2c}$ are each independently hydrogen, halogen, —$OR^{2f}$, or —$NR^{2f}R^{2g}$; $R^{2d}$ and $R^{2c}$ are each independently —OH, —OC(O)$R^{2f}$, —$OR^{2f}$, $C_{1-20}$ alkyl, $C_{2-20}$ alkenyl or $C_{2-20}$ alkynyl; alternatively, $R^{2d}$ and $R^{1a}$ are combined with the atoms to which they are attached to form a $C_{6-12}$ heterocycloalkyl; alternatively, $R^{2d}$ and $R^{1b}$ are combined with the atoms to which they are attached to form a $C_{5-12}$ heterocycloalkyl; $R^{2f}$ and $R^{2g}$ are each independently hydrogen, $C_{1-20}$ alkyl, $C_{2-20}$ alkenyl or $C_{2-20}$ alkynyl; dashed lines a, b, and c are each independently absent or a bond, wherein when n is 2, dashed line a is absent, wherein when $R^{1b}$ is oxygen and not combined with $R^{1a}$ to form an epoxide ring, dashed line b is the bond, and wherein when $R^{1c}$ is oxygen, dashed line c is the bond; and dashed circle d is absent or is 1, 2, or 3 bonds.

In another embodiment, the present invention provides a method of reducing the frequency of seizures, comprising administering to a subject in need thereof, a therapeutically effective amount of a compound of the present invention, or a pharmaceutically acceptable salt thereof, without inducing hypnotic effects in the subject, thereby reducing the frequency of seizures.

In another embodiment, the present invention provides a method of reducing hypnotic effects of cannabidiol treatment of seizures, comprising administering to a subject in need thereof, a therapeutically effective amount of a compound of the present invention, or a pharmaceutically acceptable salt thereof, thereby reducing hypnotic effects of cannabidiol treatment of seizures.

In another embodiment, the present invention provides a compound of Formula IA-1:

(IA-1)

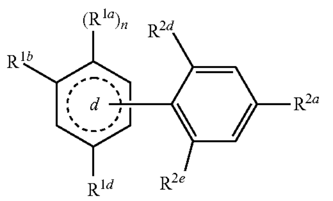

wherein n is 1 or 2; $R^{1a}$ is-$CO_2R^{1c}$, $C_{1-20}$ alkyl, $C_{2-20}$ alkenyl or $C_{2-20}$ alkynyl; $R^{1b}$ is hydrogen or oxygen; alternatively, when $R^{1b}$ is oxygen, $R^{1b}$ is combined with $R^{1a}$ and the atoms to which they are attached to form an epoxide ring; $R^{1d}$ is $C_{1-20}$ alkyl, $C_{2-20}$ alkenyl or $C_{2-20}$ alkynyl; $R^{2a}$ is —$OR^{2d}$, $C_{1-20}$ alkyl, $C_{2-20}$ alkenyl or $C_{2-20}$ alkynyl; $R^{2d}$ and $R^{2c}$ are each independently —OH, —OC(O)$R^{2f}$, —O—$C_{1-6}$ alkyl, —O—$C_{2-6}$ alkenyl, —O—$C_{2-6}$ alkynyl, $C_{1-20}$ alkyl, $C_{2-20}$ alkenyl or $C_{2-20}$ alkynyl; $R^{2f}$ is hydrogen, $C_{1-20}$ alkyl, $C_{2-20}$ alkenyl or $C_{2-20}$ alkynyl; and dashed circle d is absent or is 1, 2, or 3 bonds wherein when $R^{1a}$ is methyl, $R^{1d}$ is isopropyl, $R^{2d}$ and $R^{2c}$ are both-OH, and $R^{2a}$ is $C_{1-20}$ alkyl, then the compound is not

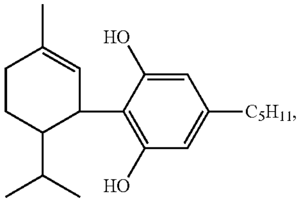

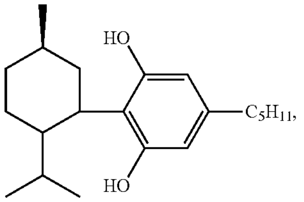

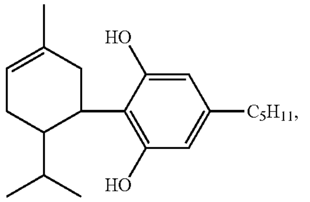

and

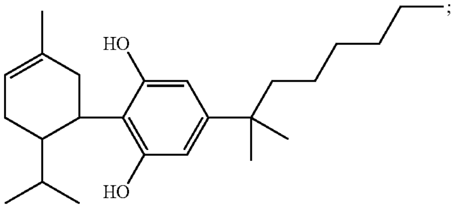

;

and wherein when $R^{1a}$ is methyl, $R^{1d}$ is propyl, $R^{2b}$ is pentyl, and $R^{2a}$ and $R^{2c}$ are both-OH, then the compound is not

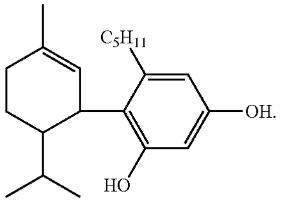

BRIEF DESCRIPTION OF THE DRAWINGS

(FIG. 2C) brain and (FIG. 2**D) blood concentrations of H2CBD (50, 100 & 200 mg/kg) and CBD (200 mg/kg) assessed via post-mortem samples obtained 90 minutes after cannabinoid administration. n>5 animals per group. Plots show median (middle bars), interquartile range (upper and lower bars) and individual animal (•) results. *=P<0.05; **=P<0.01.

DETAILED DESCRIPTION

I. General

Figure 1:
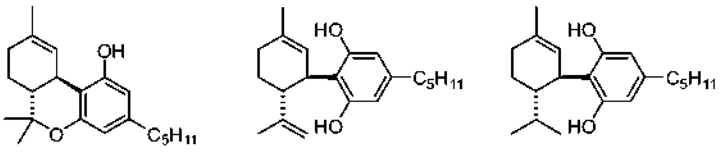
FIG. 1 shows chemical structures of THC, CBD, and H2CBD.

The present invention provides a method of treating or mitigating seizure, as well as a method of reducing the frequency of seizures, and reducing the hypnotic effects of cannabidiol treatment of seizures using H2CBD and analogs thereof. The present invention also provides new cannabidiol derivatives.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-8}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" refers to a saturated ring system having from 3 to 12 ring members and from 1 to 4 heteroatoms of N, O and S. The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (–0), among many others.

"Epoxide" refers to a three-atom cyclic ether with the following structure:

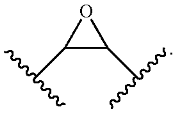 [SMILES: *C1OC1*]

"Halogen" refers to fluorine, chlorine, bromine and iodine.

"Isomers" refers to compounds with same chemical formula but different connectivity between the atoms in the molecule, leading to distinct chemical structures. Isomers include structural isomers and stereoisomers. Examples of structural isomers include, but are not limited to tautomers and regioisomers. Examples of stereoisomers include but are not limited to diastereomers and enantiomers.

"Pharmaceutically acceptable salt" refers to a compound in salt form, wherein the compound are suitable for administration to a subject. Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

"Cannabidiol" which is also known as CBD, refers to a compound with the following structure:

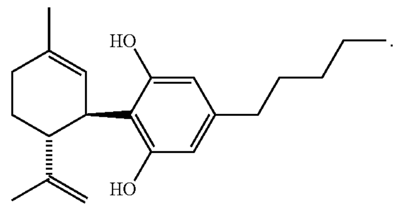 [SMILES: C=C(C)[C@@H]1CCC(C)=C[C@H]1c1c(O)cc(CCCCC)cc1O]

"H2CBD" or "dihydrocannabidiol" refers to a compound with the following structure:

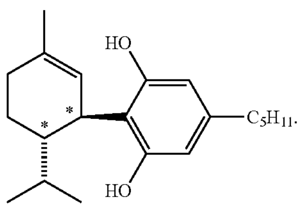

"Hypnotic effects" or "narcotic effects" refers to inducing sleep. Drugs which can cause hypnotic effects include psychoactive drugs which can induce sleep. Types of hypnotic drugs include, but are not limited to, cannibinoids, benzodiazepines, quinazolinones, imidazopyridines, and barbiturates.

"Subject" refers to animals such as mammals, including, but not limited to, primates (e.g. humans), cows, sheep, goats, horses, dogs, cats, rabbits, rats, mice and the like. In certain embodiments, the subject is a human.

"Mitigating" refers to a reduction in the severity of, or the weakening of a condition or symptom.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter; including, e.g., the result of a physical examination.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see. e.g., Lieberman, *Pharmaceutical Dosage Forms* (vols. 1-3, 1992); Lloyd, *The Art. Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

"Subject" refers to animals such as mammals, including, but not limited to, primates (e.g., humans), cows, sheep, goats, horses, dogs, cats, rabbits, rats, mice and the like. In certain embodiments, the subject is a human. In some embodiments, the subject is a companion animal.

III. Method of Treatment

The compounds of the present invention can be used for treating or mitigating a seizure. The compounds of the present invention can also be used for reducing the frequency of seizures. The compounds of the present invention can also be used for reducing the hypnotic effects of cannabidiol treatment of seizures.

In some embodiments, the compounds of the present invention are used for treating or mitigating convulsant effects. In some embodiments, the compounds of the present invention are used for treating or mitigating seizures. In some embodiments, the compounds of the present invention are used for treating or mitigating epilepsy. In some embodiments, the compounds of the present invention have anti-convulsant properties.

A. Method of Treating or Mitigating Seizure

In some embodiments, the present invention provides a method of treating or mitigating epilepsy or a seizure, comprising administering to a subject in need thereof, a therapeutically effective amount of a low abuse potential cannabinoid.

In some embodiments, the present invention provides a method of treating or mitigating epilepsy or a seizure, comprising administering to a subject in need thereof, a therapeutically effective amount of a compound of the present invention. In some embodiments, the present invention provides a method of treating or mitigating a seizure, comprising administering to a subject in need thereof, a therapeutically effective amount of a compound of the present invention.

In some embodiments, the present invention provides a method of treating or mitigating a seizure, comprising administering to a subject in need thereof, a therapeutically effective amount of a compound of Formula I:

(I)

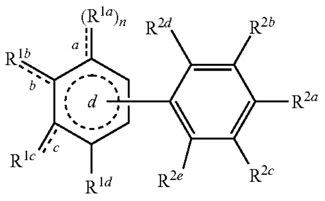

or a pharmaceutically acceptable salt thereof, without inducing hypnotic effects in the subject, thereby treating the seizure, wherein: n is 1 or 2; $R^{1a}$ and $R^{1d}$ are each independently —$CO_2R^{1c}$, $C_{1-20}$ alkyl, $C_{2-20}$ alkenyl or $C_{2-20}$ alkynyl, wherein at least one of $R^{1a}$ or $R^{1d}$ is methyl or isopropyl; $R^{1b}$ and $R^{1c}$ are each independently hydrogen or oxygen; alternatively, when $R^{1b}$ is oxygen, $R^{1b}$ is combined with $R^{1a}$ and the atoms to which they are attached to form an epoxide ring; alternatively, $R^{1b}$ is combined with $R^{1d}$ and the atoms to which they are attached to form a $C_{4-8}$ cycloalkyl, wherein the cycloalkyl is substituted with 1-3 $R^{1c}$ groups; $R^{1c}$ is H, $C_{1-20}$ alkyl, $C_{2-20}$ alkenyl or $C_{2-20}$ alkynyl; $R^{2a}$ is —$OR^{2f}$, $C_{1-20}$ alkyl, $C_{2-20}$ alkenyl or $C_{2-20}$ alkynyl; $R^{2b}$ and $R^{2c}$ are each independently hydrogen, halogen, —$OR^{2f}$, or —$NR^{2f}R^{2g}$; $R^{2d}$ and $R^{2c}$ are each independently —OH, —$OC(O)R^{2f}$, —$OR^{2f}$, $C_{1-20}$ alkyl, $C_{2-20}$ alkenyl or $C_{2-20}$ alkynyl; alternatively, $R^{2d}$ and $R^{1a}$ are combined with the atoms to which they are attached to form a $C_{6-12}$ heterocycloalkyl; alternatively, $R^{2d}$ and $R^{1b}$ are combined with the atoms to which they are attached to form a $C_{5-12}$ heterocycloalkyl; $R^{2f}$ and $R^{2g}$ are each independently hydrogen, $C_{1-20}$ alkyl, $C_{2-20}$ alkenyl or $C_{2-20}$ alkynyl; dashed lines a, b, and c are each independently absent or a bond, wherein when n is 2, dashed line a is absent, wherein when $R^{1b}$ is oxygen and not combined with $R^{1a}$ to form an epoxide ring, dashed line b is the bond, and wherein when $R^{1c}$ is oxygen, dashed line c is the bond; and dashed circle d is absent or is 1, 2, or 3 bonds.

In some embodiments, the present invention provides method of treating or mitigating a seizure, comprising administering to a subject in need thereof, a therapeutically effective amount of a compound of Formula I:

(I)

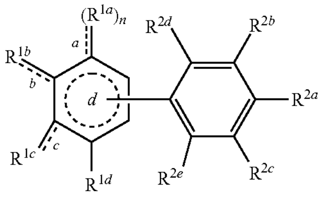

or a pharmaceutically acceptable salt thereof, without inducing hypnotic effects in the subject, thereby treating the seizure, wherein: n is 1 or 2; $R^{1a}$ and $R^{1d}$ are each independently —$COR^{1c}$, $C_{1-20}$ alkyl, $C_{2-20}$ alkenyl or $C_{2-20}$ alkynyl, wherein at least one of $R^{1a}$ or $R^{1d}$ is methyl or isopropyl; $R^{1b}$ and $R^{1c}$ are each independently hydrogen or oxygen; alternatively, when $R^{1b}$ is oxygen, $R^{1b}$ is combined with $R^{1a}$ and the atoms to which they are attached to form an epoxide ring; alternatively, $R^{1b}$ is combined with $R^{1d}$ and the atoms to which they are attached to form a $C_{4-8}$ cycloalkyl, wherein the cycloalkyl is substituted with 1-3 $R^{1c}$ groups; $R^{1c}$ is H, $C_{1-20}$ alkyl, $C_{2-20}$ alkenyl or $C_{2-20}$ alkynyl; $R^{2a}$ is —$OR^{2f}$, $C_{1-20}$ alkyl, $C_{2-20}$ alkenyl or $C_{2-20}$ alkynyl; $R^{2b}$ and $R^{2c}$ are each independently hydrogen, halogen, —$OR^{2f}$, or —$NR^{2f}R^{2g}$; $R^{2d}$ and $R^{2c}$ are each independently —OH, —$OC(O)R^{2f}$, —O—$C_{1-6}$ alkyl, —O—$C_{2-6}$ alkenyl, —O—$C_{2-6}$ alkynyl, $C_{1-20}$ alkyl, $C_{2-20}$ alkenyl or $C_{2-20}$ alkynyl; $R^{2f}$ and $R^{2g}$ are each independently hydrogen, $C_{1-20}$ alkyl, $C_{2-20}$ alkenyl or $C_{2-20}$ alkynyl; dashed lines a, b, and c are each independently absent or a bond, wherein when n is 2, a is absent, wherein when $R^{1b}$ is oxygen and not combined with $R^{1a}$ to form an epoxide ring, dashed line b is the bond, and wherein when $R^{1c}$ is oxygen, dashed line c is the bond; and dashed circle d is absent or is 1 or 2 bonds.

In some embodiments, n is 1 or 2. In some embodiments, n is 1. In some embodiments, n is 2.

In some embodiments, $R^{1a}$ and $R^{1d}$ are each independently —$CO_2R^{1c}$, $C_{1-20}$ alkyl, $C_{2-20}$ alkenyl or $C_{2-20}$ alkynyl, wherein at least one of $R^{1a}$ or $R^{1d}$ is methyl or isopropyl; $R^{1b}$ and $R^{1c}$ are each independently hydrogen or oxygen; alternatively, when $R^{1b}$ is oxygen, $R^{1b}$ is combined with $R^{1a}$ and the atoms to which they are attached to form an epoxide ring; alternatively, $R^{1b}$ is combined with $R^{1d}$ and the atoms to which they are attached to form a $C_{4-8}$ cycloalkyl, wherein the cycloalkyl is substituted with 1-3 $R^{1c}$ groups; and $R^{1c}$ is H, $C_{1-20}$ alkyl, $C_{2-20}$ alkenyl or $C_{2-20}$ alkynyl.

In some embodiments, $R^{1a}$ and $R^{1d}$ are each independently —$CO_2R^{1c}$, $C_{1-20}$ alkyl, $C_{2-20}$ alkenyl or $C_{2-20}$ alkynyl. In some embodiments, $R^{1a}$ and $R^{1d}$ are each independently $C_{1-20}$ alkyl, $C_{2-20}$ alkenyl or $C_{2-20}$ alkynyl. In some embodiments, $R^{1a}$ and $R^{1d}$ are each independently $C_{1-20}$ alkyl or $C_{2-20}$ alkenyl. In some embodiments, $R^{1a}$ and $R^{1d}$ are each independently methyl, ethyl, propyl, isopropyl, butyl, isobutyl, sec-butyl, tert-butyl, or pentyl. In some embodiments, $R^{1a}$ and $R^{1d}$ are each independently methyl, ethyl, propyl, or isopropyl. In some embodiments, $R^{1a}$ is methyl. In some embodiments, $R^{1d}$ is isopropyl. In some embodiments, $R^{1a}$ is methyl and $R^{1d}$ is isopropyl.

In some embodiments, $R^{1b}$ and $R^{1c}$ are each independently hydrogen or oxygen. In some embodiments, $R^{1b}$ is oxygen, or $R^{1b}$ is combined with $R^{1a}$ and the atoms to which they are attached to form an epoxide ring. In some embodiments, $R^{1b}$ is combined with $R^{1d}$ and the atoms to which they are attached to form a $C_{4-8}$ cycloalkyl. In some embodiments, $R^{1b}$ is oxygen. In some embodiments, $R^{1b}$ is hydrogen. In some embodiments, $R^{1c}$ is oxygen. In some embodiments, $R^{1c}$ is hydrogen.

In some embodiments, $R^{2a}$ is-$OR^{2f}$, $C_{1-20}$ alkyl, $C_{2-20}$ alkenyl or $C_{2-20}$ alkynyl; $R^{2b}$ and $R^{2c}$ are each independently hydrogen, halogen, —$OR^{2f}$, or —$NR^{2f}R^{2g}$; $R^{2d}$ and $R^{2c}$ are each independently —OH, —$OC(O)R^{2f}$, —$OR^{2f}$, $C_{1-20}$ alkyl, $C_{2-20}$ alkenyl or $C_{2-20}$ alkynyl; and $R^{2f}$ and $R^{2g}$ are each independently hydrogen, $C_{1-20}$ alkyl, $C_{2-20}$ alkenyl or $C_{2-20}$ alkynyl.

In some embodiments, $R^{2a}$ is-$OR^{2f}$, $C_{1-20}$ alkyl, $C_{2-20}$ alkenyl or $C_{2-20}$ alkynyl. In some embodiments, $R^{2a}$ is $C_{1-20}$ alkyl, $C_{2-20}$ alkenyl or $C_{2-20}$ alkynyl. In some embodiments, $R^{2a}$ is $C_{1-20}$ alkyl. In some embodiments, $R^{2a}$ is $C_{4-15}$ alkyl. In some embodiments, $R^{2a}$ is $C_{4-10}$ alkyl. In some embodiments, $R^{2a}$ is butyl, pentyl, isopentyl, hexyl, 2-methylhex-2-yl, heptyl, 3-methylhept-2-yl, or octyl. In some embodiments, $R^{2a}$ is pentyl, isopentyl, hexyl, 2-methylhex-2-yl, heptyl, or 3-methylhept-2-yl.

In some embodiments, $R^{2b}$ and $R^{2c}$ are each independently hydrogen, halogen, —$OR^{2f}$, or —$NR^{2f}R^{2g}$. In some embodiments, $R^{2b}$ and $R^{2c}$ are each independently hydrogen, halogen, or —$OR^{2f}$. In some embodiments, $R^{2b}$ and $R^{2c}$ are each independently hydrogen, F, Cl, —OH, or —O—$C_{1-6}$alkyl. In some embodiments, $R^{2b}$ and $R^{2c}$ are each independently hydrogen or F. In some embodiments $R^{2b}$ and $R^{2c}$ are both hydrogen. In some embodiments, $R^{2b}$ and $R^{2c}$ are both F.

In some embodiments, $R^{2d}$ and $R^{2c}$ are each independently —OH, —$OC(O)R^{2f}$, —$OR^{2f}$, $C_{1-20}$ alkyl, $C_{2-20}$ alkenyl or $C_{2-20}$ alkynyl. In some embodiments, $R^{2d}$ and $R^{2c}$ are each independently —OH, —$OC(O)R^{2f}$, or —$OR^{2f}$. In some embodiments, $R^{2d}$ and $R^{2c}$ are each independently —OH, —OC(O)Me, —OC(O)Et, —OMe, —OEt, —OPr, or —OBu. In some embodiments, $R^{2d}$ and $R^{2c}$ are each independently —OH, —OC(O)Me, or —OMe. In some embodiments, $R^{2d}$ and $R^{2c}$ are both-OH.

In some embodiments, $R^{2f}$ and $R^{2g}$ are each independently hydrogen, $C_{1-20}$ alkyl, $C_{2-20}$ alkenyl or $C_{2-20}$ alkynyl. In some embodiments, $R^{2f}$ and $R^{2g}$ are each independently hydrogen, $C_{1-20}$ alkyl, or $C_2$-20 alkenyl. In some embodiments, $R^{2f}$ and $R^{2g}$ are each independently hydrogen or $C_{1-20}$ alkyl. In some embodiments, $R^{2f}$ and $R^{2g}$ are each independently hydrogen, methyl, ethyl, propyl, or isopropyl. In some embodiments, $R^{2f}$ and $R^{2g}$ are each independently hydrogen or methyl. In some embodiments, $R^{2f}$ and $R^{2g}$ are both hydrogen. In some embodiments, $R^{2f}$ and $R^{2g}$ are both methyl.

In some embodiments, dashed lines a, b, and c are each independently absent or a bond, wherein when n is 2, dashed line a is absent, wherein when $R^{1b}$ is oxygen and not combined with $R^{1a}$ to form an epoxide ring, dashed line b is the bond, and wherein when $R^{1c}$ is oxygen, dashed line c is the bond.

In some embodiments, dashed line a is absent or a bond. In some embodiments, a is absent. In some embodiments, when n is 2, a is absent. In some embodiments, dashed line b is absent or a bond. In some embodiments, b is absent. In some embodiments, b is a bond. In some embodiments, when $R^{1b}$ is oxygen and not combined with $R^{1a}$ to form an epoxide ring, dashed line b is the bond. In some embodiments, dashed line c is absent or a bond. In some embodiments, c is absent. In some embodiments, c is a bond. In some embodiments, when $R^{1c}$ is oxygen, dashed line c is the bond.

In some embodiments, dashed circle d is absent or is 1, 2, or 3 bonds. In some embodiments, dashed circle d is absent or is 1 or 2 bonds. In some embodiments, dashed circle d is absent or is 1 bond. In some embodiments, dashed circle d is absent. In some embodiments, dashed circle d is 1 bond. In some embodiments, dashed circle d is 2 bonds. In some embodiments, dashed circle d is 3 bonds.

In some embodiments, the present invention provides a method, where the compound is Formula Ia:

(Ia)

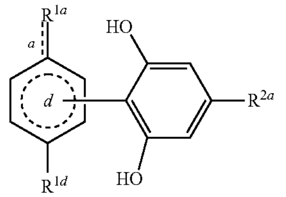

or a pharmaceutically acceptable salt thereof.

In some embodiments, the present invention provides a method, wherein the compound is Formula Ib:

(Ib)

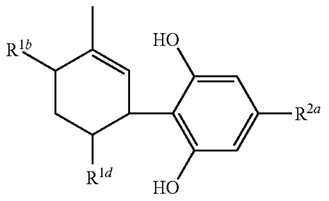

or a pharmaceutically acceptable salt thereof.

In some embodiments, the present invention provides a method, wherein the compound is Formula Ic:

(Ic)

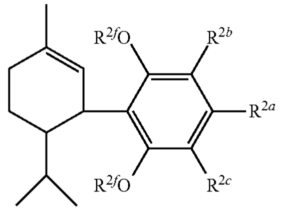

or a pharmaceutically acceptable salt thereof.

In some embodiments, the present invention provides a method, wherein the compound is Formula Id:

(Id)

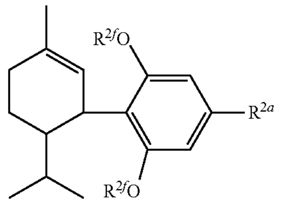

or a pharmaceutically acceptable salt thereof.

In some embodiments, the present invention provides a method, wherein the compound is Formula Ie:

(Ie)

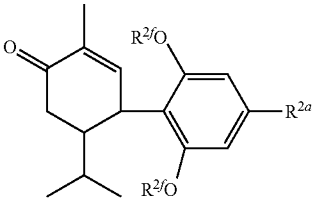

or a pharmaceutically acceptable salt thereof.

In some embodiments, the present invention provides a method, wherein the compound is Formula If:

(If)

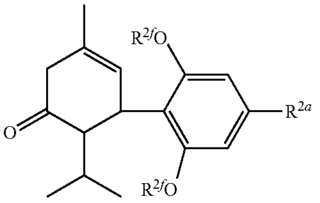

or a pharmaceutically acceptable salt thereof.

In some embodiments, the present invention provides a method, wherein the compound is Formula Ig:

(Ig)

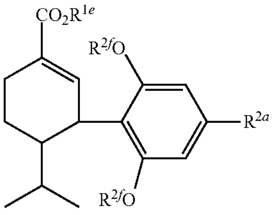

or a pharmaceutically acceptable salt thereof.

In some embodiments, the present invention provides a method, wherein the compound is Formula Ih:

(Ih)

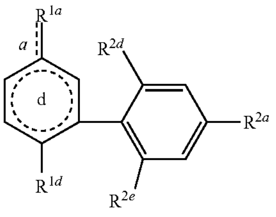

or a pharmaceutically acceptable salt thereof.

In some embodiments, the present invention provides a method, wherein the compound is Formula Ii:

(Ii)

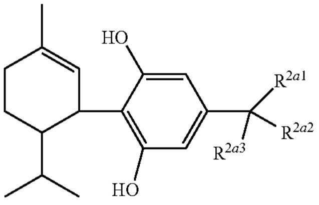

or a pharmaceutically acceptable salt thereof, wherein $R^{2a1}$, $R^{2a2}$ and $R^{2a3}$ are each independently $C_{1-19}$ alkyl, $C_{2-19}$ alkenyl or $C_{2-19}$ alkynyl. In some embodiments, $R^{2a1}$, $R^{2a2}$ and $R^{2a3}$ are each independently $C_{1-19}$ alkyl. In some embodiments, $R^{2a1}$, $R^{2a2}$ and $R^{2a3}$ are each independently $C_{1-10}$ alkyl. In some embodiments, $R^{2a1}$, $R^{2a2}$ and $R^{2a3}$ are each independently $C_{1-5}$ alkyl.

In some embodiments, the present invention provides a method, wherein the compound is Formula Ij:

(Ij)

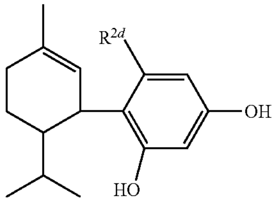

or a pharmaceutically acceptable salt thereof, wherein $R^{2d}$ is $C_{1-20}$ alkyl, $C_{2-20}$ alkenyl or $C_{2-20}$ alkynyl.

In some embodiments, the present invention provides a method, wherein the compound is Formula Ik:

(Ik)

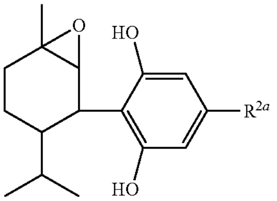

or a pharmaceutically acceptable salt thereof, wherein $R^{2a}$ is $C_{1-20}$ alkyl, $C_{2-20}$ alkenyl or $C_{2-20}$ alkynyl.

In some embodiments, the present invention provides a method, wherein the compound is:

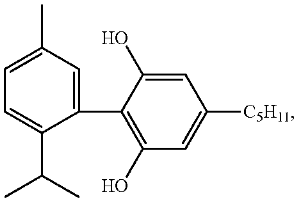

-continued

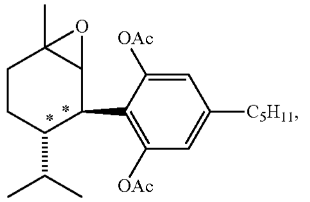

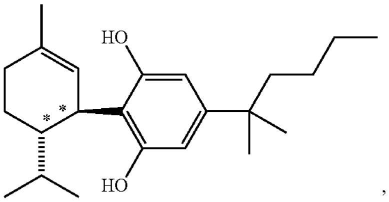

,

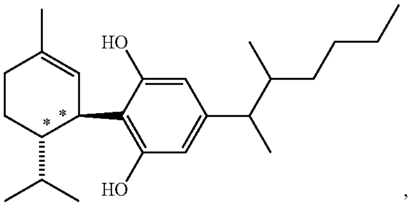

, or

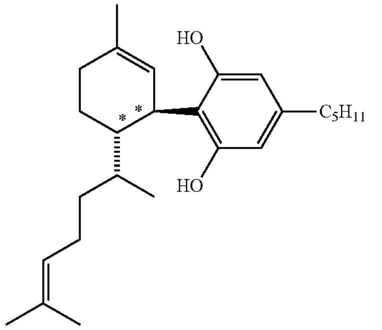

or a pharmaceutically acceptable salt thereof.

In some embodiments, the present invention provides a method, wherein the compound of Formula I is 8,9-dihydrocannabidiol:

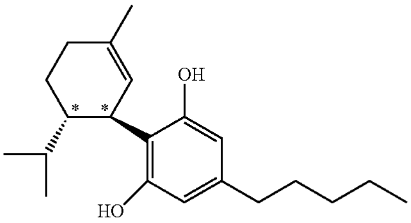 [SMILES: CCCCCc1cc(O)c([C@@H]2C=C(C)CC[C@H]2C(C)C)c(O)c1]

or a pharmaceutically acceptable salt thereof.

In some embodiments, electroencephalogram (EEG), high-density EEG, computerized tomography (CT) scan, magnetic resonance imaging (MRI), functional MRI (fMRI), positron emission tomography (PET), single-photo emission computerized tomography (SPECT), subtraction ictal SPECT coregistering to MRI (SISCOM), stastical parametric mapping (SPMJ), curry analysis, and magnetoencephalography (MEG) can be used to determine treating or mitigating a seizure.

In some embodiments, animal seizure models can be used to determine treating or mitigating a seizure. In some embodiments, the animal seizure model can be, but is not limited to, a model of generalized seizures, a model of limbic seizures, a distinct seizure model in an animal rendered epileptic by kindling, a model of ongoing seizures, and a model wherein the animal is subject to electrical shock to include tonic convulsions. In some embodiments, the animal seizure model can be, but is not limited to, a maximal PTZ seizure model, a 6 Hz model, a corneal kindled mouse model, a pilocarpine induced status epilepticus model, and a maximal electroshock model.

B. Method of Reducing Frequency of Seizures

In some embodiments, the present invention provides a method of reducing epilepsy. In some embodiments, the present invention provides a method of reducing the frequency of seizures.

In some embodiments, animal studies can be used to determine reducing the frequency of seizures. In some embodiments, animal studies include but are not limited to, rodents, rats, mice, zebrafish. In some embodiments, the animal study comprises administering a compound of the present invention about 1 hour, about 2 hours, about 3 hours, about 4 hours, or about 5 hours before administering the convulsant drug. In some embodiments, the animal study comprises administering a compound of the present invention about 1 hour before administering the convulsant drug.

In some embodiments, animal seizure models can be used to determine reducing the frequency of seizures. In some embodiments, the animal seizure model can be, but is not limited to, a model of generalized seizures, a model of limbic seizures, a distinct seizure model in an animal rendered epileptic by kindling, a model of ongoing seizures, and a model wherein the animal is subject to electrical shock to include tonic convulsions. In some embodiments, the animal seizure model can be, but is not limited to, a maximal PTZ seizure model, a 6 Hz model, a corneal kindled mouse model, a pilocarpine induced status epilepticus model, and a maximal electroshock model.

In some embodiments, the present invention provides a method of reducing the frequency of seizures, comprising administering to a subject in need thereof, a therapeutically effective amount of a compound of the present invention, or a pharmaceutically acceptable salt thereof, without inducing hypnotic effects in the subject, thereby reducing the frequency of seizures.

C. Method of Reducing Hypnotic Effects

Many cannabinoids are known to induce hypnotic effects. In some embodiments, the present invention provides a method of reducing hypnotic effects of cannabidiol treatment of epilepsy or seizures. In some embodiments, the present invention provides a method of reducing hypnotic effects of cannabidiol treatment of seizures.

In some embodiments, locomotor activity can be used to determine reducing hypnotic effects of cannabidiol treatment of epilepsy or seizures. In some embodiments, locomotor activity can be measured by, but not limited to, horizontal plane movement, vertical plane movement, and time in the center of the open field arena.

In some embodiments, administrating the compounds of the present invention results in minimal to no behavioral changes. Examples of behavioral changes include, but are not limited to, hypnotic effects and sedative effects. In some embodiments, treatment with the compound of the present invention at a high dosage results in minimal to no behavioral changes.

In some embodiments, the present invention provides a method of reducing hypnotic effects of cannabidiol treatment of seizures, comprising administering to a subject in need thereof, a therapeutically effective amount of a compound of the claimed invention, or a pharmaceutically acceptable salt thereof, thereby reducing hypnotic effects of cannabidiol treatment of seizures.

IV. Compounds

In some embodiments, the present invention provides a compound of Formula IA-1:

(IA-1)

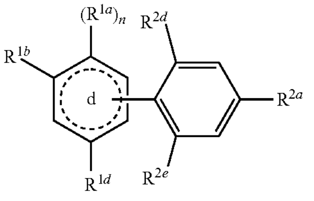

wherein n is 1 or 2; $R^{1a}$ is-$CO_2R^{1c}$, $C_{1-20}$ alkyl, $C_{2-20}$ alkenyl or $C_{2-20}$ alkynyl; $R^{1b}$ is hydrogen or oxygen; alternatively, when $R^{1b}$ is oxygen, $R^{1b}$ is combined with $R^{1a}$ and the atoms to which they are attached to form an epoxide ring; $R^{1d}$ is $C_{1-20}$ alkyl, $C_{2-20}$ alkenyl or $C_{2-20}$ alkynyl; $R^{2a}$ is-$OR^{2d}$, $C_{1-20}$ alkyl, $C_{2-20}$ alkenyl or $C_{2-20}$ alkynyl; $R^{2d}$ and $R^{2c}$ are each independently —OH, —OC(O)$R^{2f}$, —$OR^{2f}$, $C_{1-20}$ alkyl, $C_{2-20}$ alkenyl or $C_{2-20}$ alkynyl; $R^{2f}$ is hydrogen, $C_{1-20}$ alkyl, $C_{2-20}$ alkenyl or $C_{2-20}$ alkynyl; and dashed circle d is absent or is 1, 2, or 3 bonds wherein when $R^{1a}$ is methyl, $R^{1d}$ is isopropyl, $R^{2d}$ and $R^{2c}$ are both-OH, and $R^{2a}$ is $C_{1-20}$ alkyl, then the compound is not

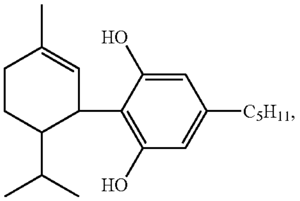

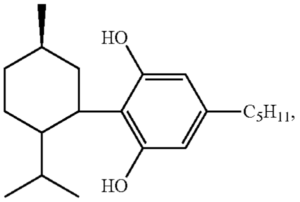

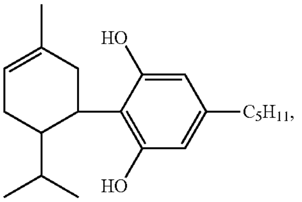

and

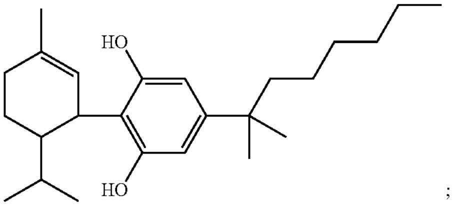

;

and wherein when $R^{1a}$ is methyl, $R^{1d}$ is propyl, $R^{2b}$ is pentyl, and $R^{2a}$ and $R^{2c}$ are both-OH, then the compound is not

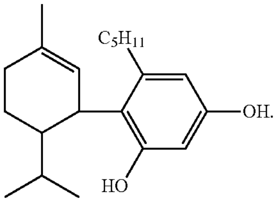

In some embodiments, when $R^{1a}$ is methyl, $R^{1d}$ is isopropyl, $R^{1d}$ and $R^{2c}$ are both-OH, and $R^{2a}$ is $C_{1-20}$ alkyl, then the compound is not

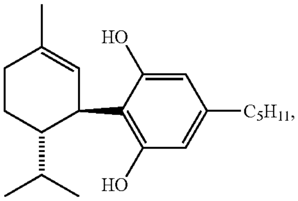

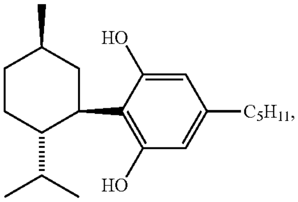

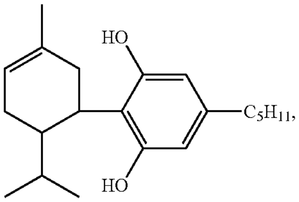

and

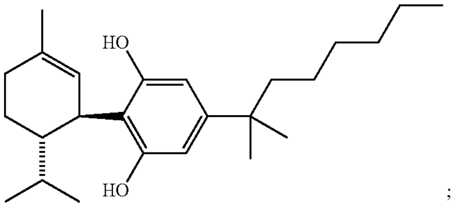

;

and wherein when $R^{1a}$ is methyl, $R^{1d}$ is propyl, $R^{2b}$ is pentyl, and $R^{2a}$ and $R^{2c}$ are both-OH, then the compound is not

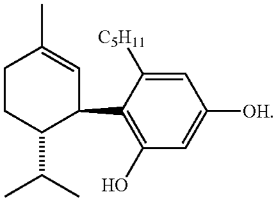

In some embodiments, n is 1 or 2. In some embodiments, n is 1. In some embodiments, n is 2.

In some embodiments, $R^{1a}$ is-$CO_2R^{1c}$, $C_{1-20}$ alkyl, $C_{2-20}$ alkenyl or $C_{2-20}$ alkynyl. In some embodiments, $R^{1a}$ is $C_{1-20}$ alkyl, $C_{2-20}$ alkenyl or $C_{2-20}$ alkynyl. In some embodiments, $R^{1a}$ is $C_{1-20}$ alkyl. In some embodiments, $R^{1a}$ is $C_{1-8}$ alkyl. In some embodiments, $R^{1a}$ is methyl, ethyl, propyl, isopropyl, butyl, iso-butyl, sec-butyl, tert-butyl, or pentyl. In some embodiments, $R^{1a}$ is methyl, ethyl, propyl, or isopropyl. In some embodiments, $R^{1a}$ is methyl.

In some embodiments, $R^{1b}$ is hydrogen or oxygen. In some embodiments, $R^{1b}$ is hydrogen. In some embodiments, $R^{1b}$ is oxygen.

In some embodiments, $R^{1d}$ is $C_{1-20}$ alkyl, $C_{2-20}$ alkenyl or $C_{2-20}$ alkynyl. In some embodiments, $R^{1d}$ is $C_{1-20}$ alkyl or $C_{2-20}$ alkenyl. In some embodiments, $R^{1d}$ is $C_{1-10}$ alkyl or $C_{2-10}$ alkenyl. In some embodiments, $R^{1d}$ is a $C_{5-8}$ alkenyl. In some embodiments, $R^{1d}$ is methyl, ethyl, propyl, isopropyl, butyl, iso-butyl, sec-butyl, tert-butyl, or pentyl. In some embodiments, $R^{1d}$ is methyl, ethyl, propyl, or isopropyl. In some embodiments, $R^{1d}$ is isopropyl. In some embodiments, $R^{1d}$ is 6-methylhept-5-en-2-yl.

In some embodiments, $R^{2a}$ is —$OR^{2d}$, $C_{1-20}$ alkyl, $C_{2-20}$ alkenyl or $C_{2-20}$ alkynyl. In some embodiments, $R^{2a}$ is $C_{1-20}$ alkyl, $C_{2-20}$ alkenyl or $C_{2-20}$ alkynyl. In some embodiments, $R^{2a}$ is $C_{1-20}$ alkyl. In some embodiments, $R^{2a}$ is $C_{4-15}$ alkyl. In some embodiments, $R^{2a}$ is $C_{4-10}$ alkyl. In some embodiments, $R^{2a}$ is butyl, pentyl, isopentyl, hexyl, 2-methylhex-2-yl, heptyl, 3-methylhept-2-yl, or octyl. In some embodiments, $R^{2a}$ is pentyl, isopentyl, hexyl, 2-methylhex-2-yl, heptyl, or 3-methylhept-2-yl.

In some embodiments, $R^{2d}$ and $R^{2c}$ are each independently —OH, —OC(O)$R^{2f}$, —$OR^{2f}$, $C_{1-20}$ alkyl, $C_{2-20}$ alkenyl or $C_{2-20}$ alkynyl; and $R^{2f}$ is hydrogen, $C_{1-20}$ alkyl, $C_{2-20}$ alkenyl or $C_{2-20}$ alkynyl.

In some embodiments, $R^{2d}$ and $R^{2c}$ are each independently —OH, —OC(O)$R^{2f}$, —$OR^{2f}$, $C_{1-20}$ alkyl; and $R^{2f}$ is $C_{1-6}$ alkyl, $C_{2-6}$ alkenyl or $C_{2-6}$ alkynyl. In some embodiments, $R^{2d}$ and $R^{2c}$ are each independently —OH, —OC(O)$R^{2f}$, or —$OR^{2f}$; and Raf is $C_{1-6}$ alkyl. In some embodiments, $R^{2d}$ and $R^{2c}$ are each independently —OH, —OC(O)Me, —OC(O)Et, —OMe, —OEt, —OPr, or —OBu. In some embodiments, $R^{2d}$ and $R^{2c}$ are each independently —OH, —OC(O)Me, or —OMe. In some embodiments, $R^{2d}$ and $R^{2c}$ are both-OH.

In some embodiments, $R^{2f}$ is hydrogen, $C_{1-20}$ alkyl, $C_{2-20}$ alkenyl or $C_{2-20}$ alkynyl. In some embodiments, $R^{2f}$ is hydrogen, $C_{1-20}$ alkyl, or $C_2$-20 alkenyl. In some embodiments, $R^{2f}$ is hydrogen or $C_{1-20}$ alkyl. In some embodiments, $R^{2f}$ is hydrogen or $C_{1-10}$ alkyl. In some embodiments, $R^{2f}$ is hydrogen, methyl, ethyl, propyl, or isopropyl. In some embodiments, $R^{2f}$ is hydrogen or methyl. In some embodiments, $R^{2f}$ is hydrogen. In some embodiments, $R^{2f}$ is methyl.

In some embodiments, dashed circle d is absent or is 1, 2, or 3 bonds. In some embodiments, dashed circle d is absent or is 1 or 2 bonds. In some embodiments, dashed circle d is absent or is 1 bond. In some embodiments, dashed circle d is absent. In some embodiments, dashed circle d is 1 bond. In some embodiments, dashed circle d is 2 bonds. In some embodiments, dashed circle d is 3 bonds.

In some embodiments, the present invention provides a compound, wherein the compound is Formula (IA-1a):

(IA-1a)

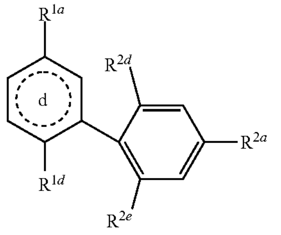

or a pharmaceutically acceptable salt thereof.

In some embodiments, the present invention provides a compound, wherein the compound is Formula (IA-1b):

(IA-1b)

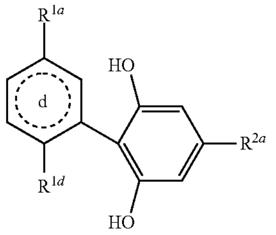

or a pharmaceutically acceptable salt thereof.

In some embodiments, the present invention provides a compound, wherein the compound is Formula (IA-1c):

(IA-1c)

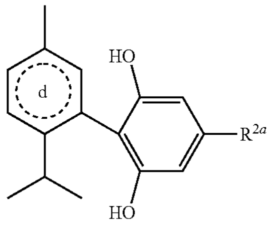

or a pharmaceutically acceptable salt thereof.

In some embodiments, the present invention provides a compound, wherein the compound is Formula (IA-1d):

(IA-1d)

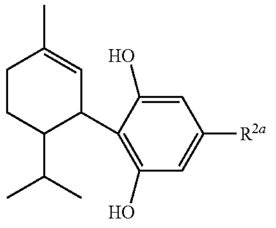

or a pharmaceutically acceptable salt thereof.

In some embodiments, the present invention provides a compound, wherein the compound is Formula (IA-1e):
(IA-1e)
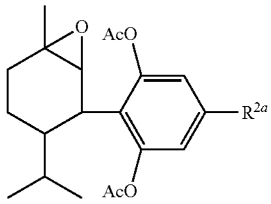
or a pharmaceutically acceptable salt thereof.
In some embodiments, compounds of the present invention include, but are not limited to:
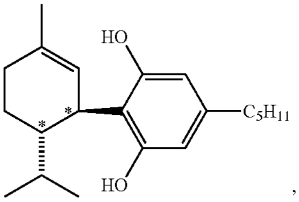
,
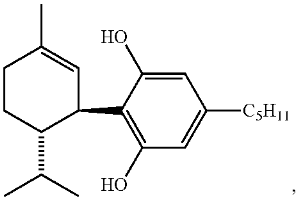
,
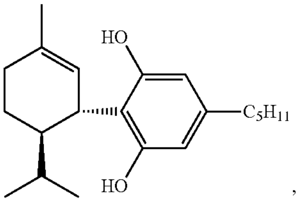
,
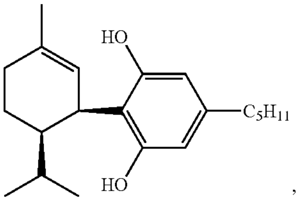
,
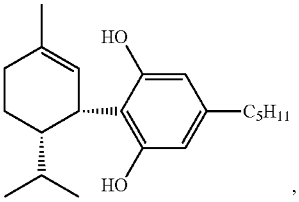
,
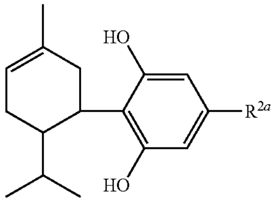
,
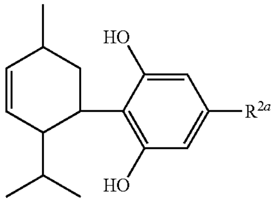
,
-continued
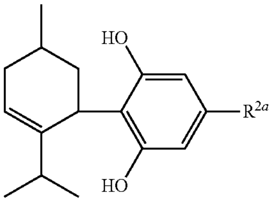
,
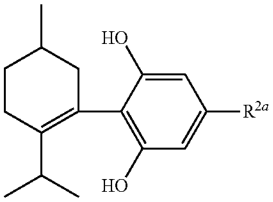
,
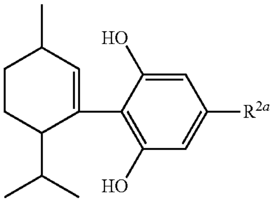
,
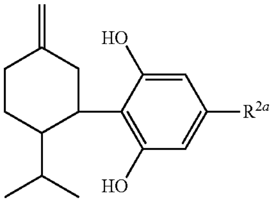
,
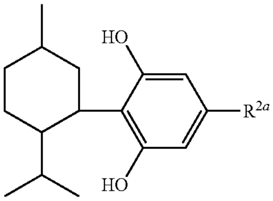
,
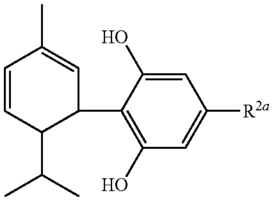
,
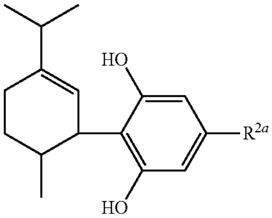
,
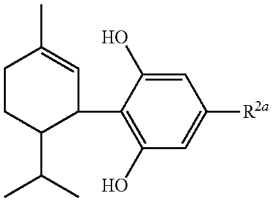
,
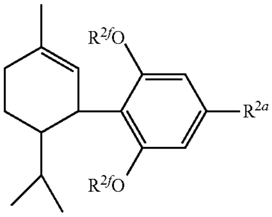
,
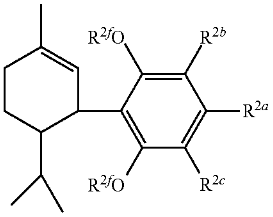
,
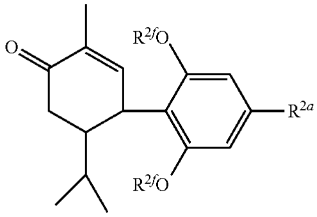
,
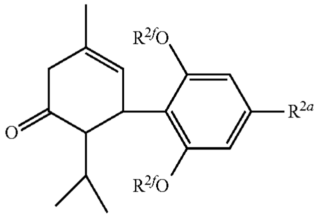
,
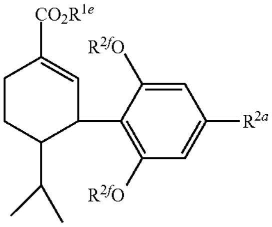
, -continued
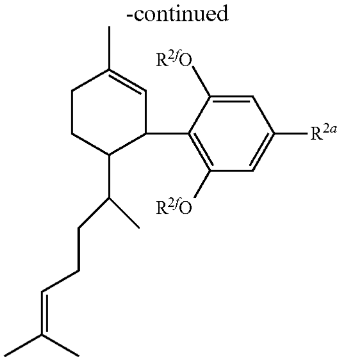
,
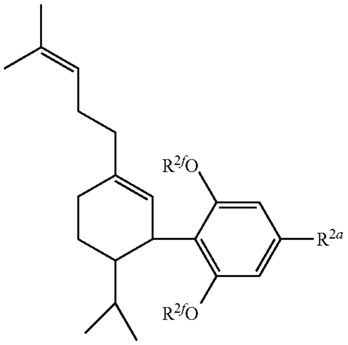
,
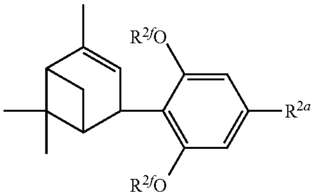
,
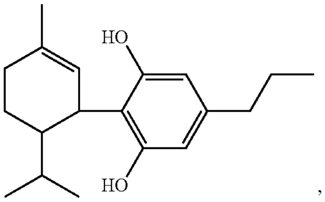
,
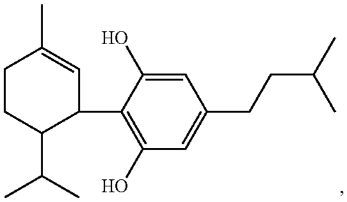
,
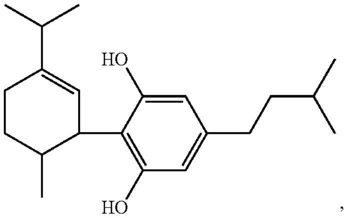
,
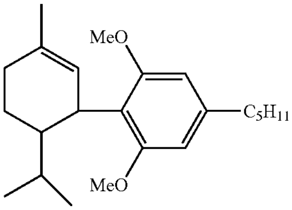
,
-continued
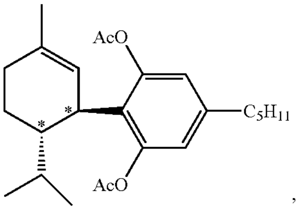
,
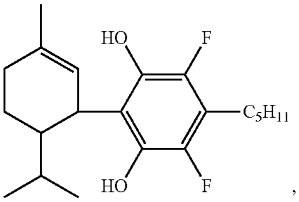
,
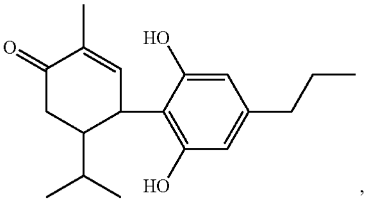
,
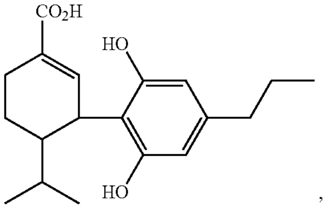
,
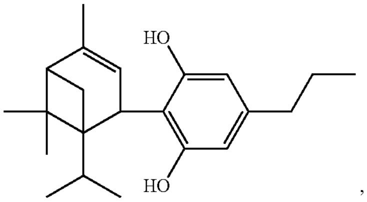
,
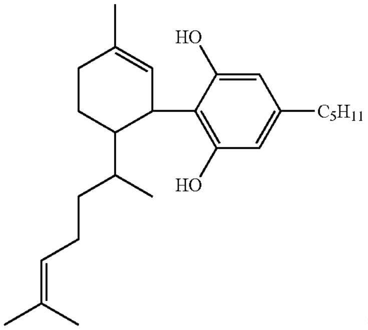
,
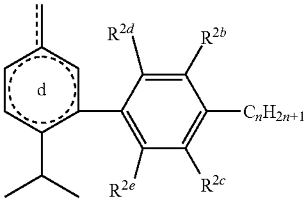
, -continued
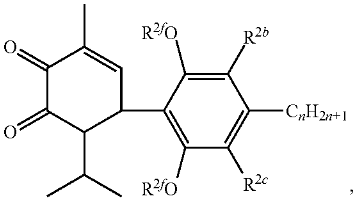,
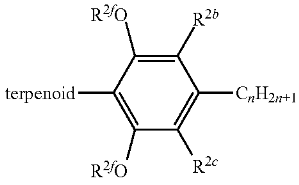,
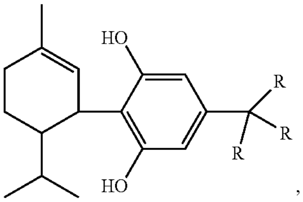,
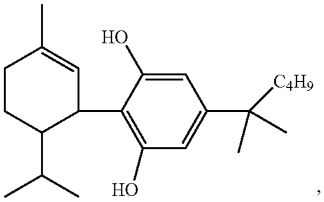,
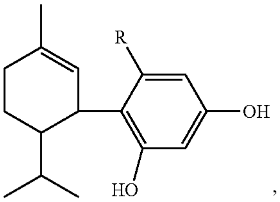, 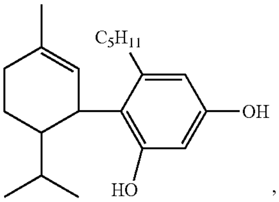,
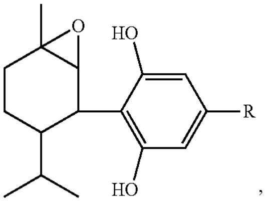, 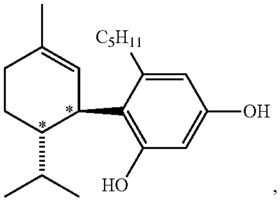,
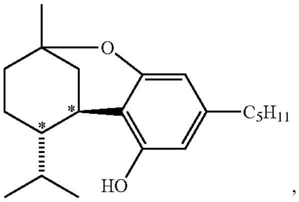,
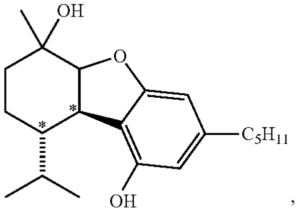,
-continued
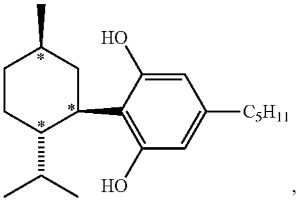,
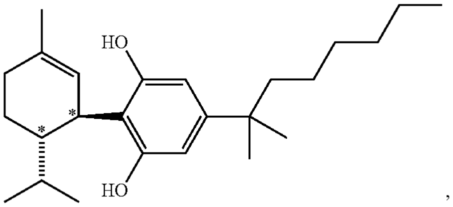,
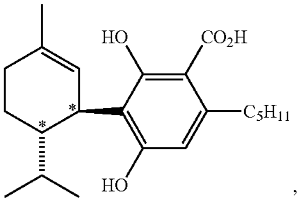,
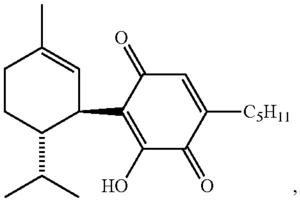,
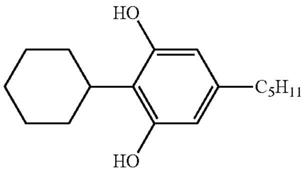,
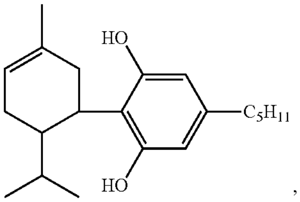,
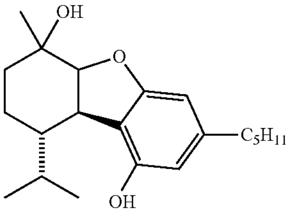,
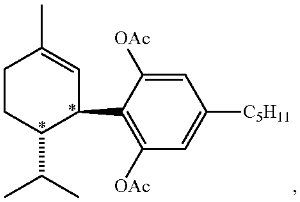, -continued

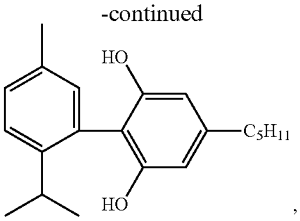

,

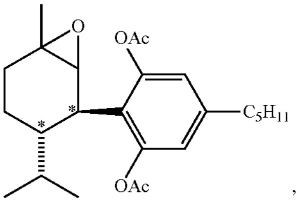

,

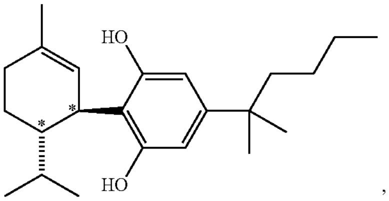

,

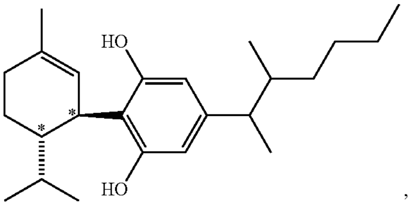

, and

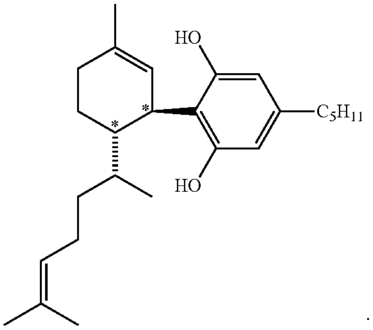

.

In some embodiments, the present invention provides a compound, or a pharmaceutically acceptable salt thereof, wherein the compound is:

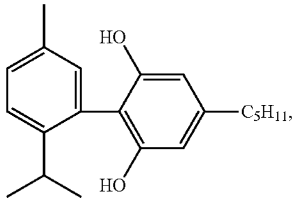

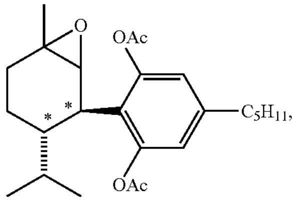

-continued

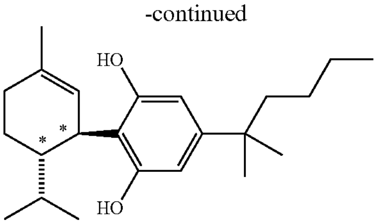

,

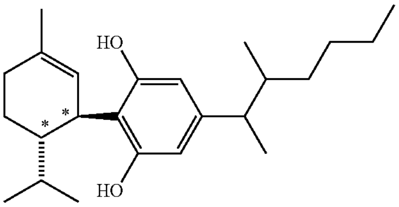

, or

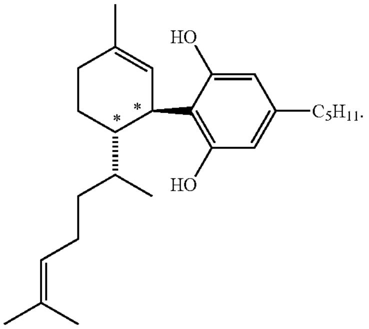

V. Formulation and Administration

The compositions of the present invention can be prepared in a wide variety of oral, parenteral, thin film, and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). The composition of this invention can also be administered by thin film drug delivery methods.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

The compounds of the present invention can also be in the salt forms, such as acid or base salts of the compounds of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

VI. Examples

For compounds of the present invention which display an asterisk (*) adjacent to a stereocenter, the indicated stereochemistry shows the relative stereochemistry at the identified atoms, but not the absolute stereochemistry. For example, for the H2CBD compound shown below:

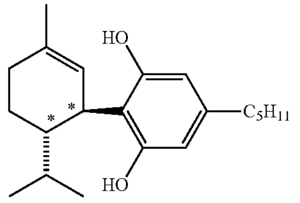

the asterisk (*) indicates that the compound is trans across the indicated atoms, and can be either the (S,S) or (R,R) enantiomer, or a mixture thereof:

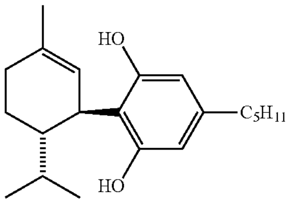

and

S,S

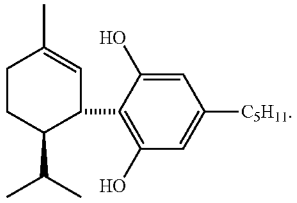

R,R

In another example, for the H4CBD compound shown below:

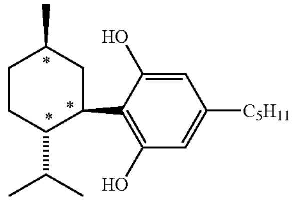

the asterisk (*) indicates that the compound can be in either stereoisomeric form, with retention to relative stereochemistry, as indicated below:

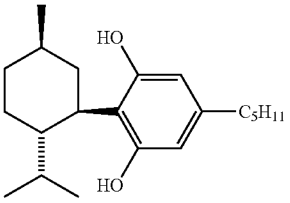

and

R,S,R

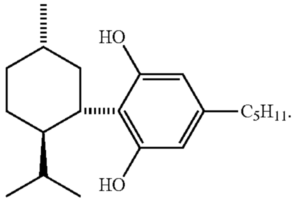

S,R,S

Other compounds of the present invention which display an asterisk (*) indicates the relative stereochemistry of the indicated atoms, but not the absolute stereochemistry as described above.

In some embodiments, the compounds which comprise an asterisk (*) can have an enantiomeric excess (ee) of 0% to 100%. In some embodiments, the ee is 0% to about 90%. In some embodiments, the ee is 0% to about 70%. In some embodiments, the ee is 0% to about 50%. In some embodiments, the ee is 0% to about 30%. In some embodiments, the ee is 0%.

Example 1. H2CBD Preparation

A solution of olivetol (1.72 g, 9.54 mmol) and food-grade α-phellandrene (1.41 g, 10.4 mmol, 1.09 eq) in benzene (5 mL) was treated with p-toluenesulfonic acid monohydrate (0.545 g, 2.87 mmol) and the mixture was allowed to stir at room temperature for 1 h. The solvent was removed in vacuo and the residue was purified by silica gel chromatography using a gradient elution (100% hexanes to 10% diethyl ether in hexanes) to give H2CBD (2.14 g, 71%) as a dark yellow oil. Spectroscopic data ($^{1}$H-NMR, $^{13}$C-NMR) were in full agreement with the literature.

Example 2. 2-(6-Isopropyl-3-methylcyclohex-2-en-1-yl)-5-pentylbenzene-1,3-diol (8,9-dihydrocannabidiol, H2CBD)

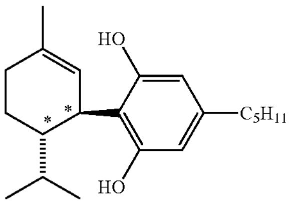

A 150 mL round-bottomed Schlenk flask was equipped with a magnetic stir bar and a rubber septum. The flask was flushed with nitrogen and olivetol (3.00 g, 16.6 mmol), toluene (50 mL), and p-toluenesulfonic acid monohydrate (190 mg, 6 mol %) were added. The flask was placed in a pre-heated (70° C.) oil bath and stirred for 15 min, after which α-phellandrene (2.80 mL, 2.38 g, 17.4 mmol) was injected through the septum within 1 min. After 25 min the reaction was quenched by pouring into a mixture of saturated aq. $NaHCO_3$ (20 mL) and ice (10 g). The organic phase was separated and the aqueous phase was extracted with ethyl acetate (2×50 mL). The combined organic phase was washed with water and brine, dried over magnesium sulfate and the solvent was evaporated to give the crude product (5.25 g). A chromatography cartridge was charged with 100 g of silica gel and equilibrated with a mixture of dichloromethane (15%) and hexane (85%). The crude product was loaded on the column and eluted with 4 column volumes the solvent mixture. The method was then changed to gradient elution, and within the next 6 column volumes the DCM content was gradually increased to 50%. The fractions containing the product were combined and the solvent was evaporated to give H2CBD (3.24 g, 62%) as a viscous, pale yellow oil. $^{1}$HNMR (400 MHZ, $CDCl_3$) δ 6.21 (br s, 3H), 5.52 (s, 1H), 4.71 (s, 1H), 3.82 (br d, J=9.8 Hz, 1H), 2.44 (t, J=7.8 Hz, 2H), 2.12-2.10 (m, 2H), 1.82-1.76 (m, 4H, incl. 1.77 s, 3H), 1.63-1.55 (m, 4H), 1.45-1.27 (m, 6H), 0.91-0.85 (m, 9H). $^{13}$C NMR (101 MHz, $CDCl_3$) δ 156.3 (br), 154.4 (br), 143.1, 140.2, 125.0, 114.1, 109.9 (br), 107.5 (br), 43.8, 35.6 (2C), 31.7, 30.85, 30.8, 28.0, 23.8, 22.7, 22.2, 21.8, 16.5, 14.2. MS (ESI): 316 [M, 18%], 273 (8%), 246 (23%), 231 (100%).

Example 3. 5-Isopropyl-2-methyl-9-pentyl-3,4,5,6-tetrahydro-2H-2,6-methano-1-benzoxocin-7-ol (8,9-dihydro-iso-THC)

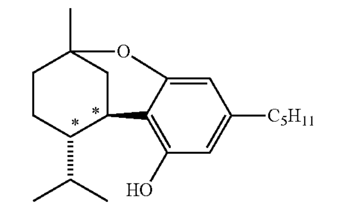

A 50 mL round-bottomed flask was charged with the olivetol (600 mg, 3.33 mmol), benzene (10 mL), p-toluenesulfonic acid monohydrate (40 mg, 6 mol %), and δ-phellandrene (0.55 mL, 470 mg, 3.5 mmol). The mixture was heated under reflux for 1 h with azeotropic removal of water using a Dean-Stark apparatus. After cooling to room temperature, the reaction was quenched into saturated aq. $NaHCO_3$, the organic phase was separated and the aqueous phase was extracted with ethyl acetate (2×10 mL). The combined organic phase was washed with water and brine, dried over magnesium sulfate, and the solvent was evaporated. The crude product was purified by vacuum distillation to give 8,9-dihydro-iso-THC (780 mg, 74%) as a colorless glass, bp 192-198° C./200 mTorr. $^{1}$H NMR (600 MHZ, $CDCl_3$) δ 6.28 (d, —4.5 I Hz, 1H), 6.12 (d, J=4.5 Hz, 1H), 4.54 (d, J=4.4 Hz, 1H), 3.33 (br q, J=2.9 Hz, 1H), 2.45 (dd, J=7.0, 3.1 Hz, 2H), 1.95-1.70 (m, 3H), 1.63-1.48 (m, 7H), 1.36-1.25 (m, 9H, incl. 1.33 s, 3H), 1.09 (t, J=6.0 Hz, 3H), 0.95 (d, J=6.0 Hz, 3H), 0.89 (d, J=5.7 Hz, 3H). $^{13}$C NMR (151 MHz, $CDCl_3$) δ 157.46, 152.08, 142.44, 111.71, 107.80, 106.05, 74.47, 44.34, 35.70, 34.98, 31.59, 30.79, 30.52, 29.35, 27.79, 26.24, 22.57, 22.07, 21.13, 20.52, 14.05. MS (ESI): 316 [M, 26%], 273 (7%), 260 (24%), 231 (100%).

Example 4. 4-(6-Isopropyl-3-methylcyclohex-2-en-1-yl)-5-pentylbenzene-1,3-diol (8,9-dihydro-o-canabidiol, iso-H2CBD)

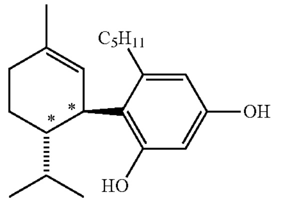

A 100 mL round-bottomed Schlenk flask was equipped with a magnetic stir bar and a rubber septum. The flask was flushed with nitrogen and olivetol (1.80 g, 10.0 mmol), toluene (30 mL), p-toluenesulfonic acid monohydrate (60 mg, 3 mol %), and α-phellandrene (1.76 mL, 1.50 g, 11.0 mmol) were added. The reaction was stirred for 6 h at room temperature and quenched with saturated aq $NaHCO_3$ (20 mL). The organic phase was separated and the aqueous phase was extracted with ethyl acetate (2×30 mL). The combined organic phase was washed with water and brine, dried over magnesium sulfate, and the solvent was evaporated to give the crude product (3.10 g). A chromatography cartridge was charged with 100 g of silica gel and equilibrated with a mixture of dichloromethane (30%) and hexane (70%). The crude product was loaded on the column and eluted with 6 CV of the solvent mixture. Fractions containing H2CBD were evaporated (1.10 g, 34%). The column was then further eluted with pure DCM, the fractions containing product were combined, and the solvent was evaporated to give iso-H2CBD (1.40 g, 44%) as viscous, pale yellow oil. $^{1}$H NMR (600 MHz, $CDCl_3$) δ 6.24 (s, 1H), 6.22 (s, 1H), 6.08 (s, 1H), 5.47 (s, 1H), 4.80 (s, 1H), 3.44 (d, J=10.8 Hz, 1H), 2.66 (ddd, J=15.0, 9.5, 6.0 Hz, 1H), 2.44-2.31 (m, 1H), 2.27-2.05 (m, 2H), 1.81-1.70 (m, 5H, incl. 1.77 s 3H), 1.56-1.48 (m, 3H), 1.37-1.30 (m, 5H), 0.91-0.87 (m, 3H), 0.84 (d, J=9.9, 3H), 0.82 (d, J=9.9, 3H). $^{13}$C NMR (151 MHz, $CDCl_3$) δ 156.56, 154.55, 144.09, 139.95, 125.13, 120.24, 108.60, 102.47, 42.93, 38.30, 34.24, 31.90, 31.29, 30.60, 27.27, 23.65, 22.57, 22.16, 21.92, 16.79, 14.07. MS (ESI): 316 [M, 42%], 246 (67%), 231 (100%), 189 (44%).

Example 5. 2-(2-Isopropyl-5-methylcyclohexyl)-5-pentylbenzene-1,3-diol (Tetrahydrocanabidiol, H4CBD)

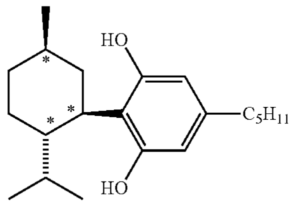

A 250 mL autoclave was equipped with a magnetic stir bar and charged with H2CBD (6.00 g, 19.0 mmol), glacial acetic acid (100 mL), and platinum oxide (150 mg). The vessel was purged with H2 and the reaction mixture was stirred under 400 psi H2 for 12 h. Methanol (100 mL) was added and the mixture was filtered through Celite. The solvent was evaporated and the residue was purified by vacuum distillation to give H4CBD (5.68 g, 94%) as colorless glass, bp 194-196° C. at 200 mTorr. $^{1}H$ NMR (600 MHZ, $CDCl_3$) δ 6.18 (s, 1H), 6.12 (s, 1H), 4.62 (d, J=3.3 Hz, 2H), 2.99 (td, J=11.4, 3.7 Hz, 1H), 2.42 (t, J=7.9 Hz, 2H), 2.09-1.96 (m, 1H), 1.86-1.46 (m, 8H), 1.36-1.25 (m, 4H), 1.12-1.02 (m, 4H), 0.91-0.86 (m, 6H), 0.84 (d, J=7.0 Hz, 3H), 0.71 (d, J=7.0 Hz, 3H). $^{13}C$ NMR (151 MHz, $CDCl_3$) δ 155.81, 154.42, 142.30, 115.46, 109.45, 108.50, 45.00, 40.56, 38.50, 35.80, 35.63, 33.89, 31.96, 30.97, 28.98, 25.75, 22.91, 22.86, 22.06, 16.13, 14.40. MS (ESI): 318 [M, 27%], 262 (12%), 233 (58%), 193 (100%).

Example 6. 2-Cyclohexyl-5-pentylbenzene-1,3-diol

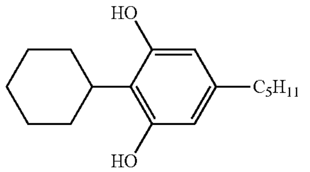

A 100 mL round-bottom flask was equipped with a magnetic stir bar and a rubber septum. The flask was charged with the olivetol (1.00 g, 5.55 mmol), cyclohexanol (1.70 g, 16.6 mmol) and 85% orthophosphoric acid (3 mL). The flask was sealed and the mixture was heated at 90° C. with stirring for 12 h. The reaction was cooled, the pressure was released, and the reaction was heated again at 130° C. for 1 h under a flow of nitrogen gas. After cooling, the reaction was quenched with water (20 mL) and extracted with ethyl acetate (3×30 mL). The combined organic phase was washed with water, saturated sodium bicarbonate solution, and brine, dried over the magnesium sulfate, and the solvent was evaporated to give the crude product (1.2 g). Column chromatography with 40:60 dichloromethane:hexane gave 2-cyclohexyl-5-pentylbenzene-1,3-diol (470 mg, 33%) as white crystalline solid, mp 57-58° C. $^{1}H$ NMR (400 MHZ, $CDCl_3$) δ 6.16 (s, 2H), 4.57 (s, 2H), 3.19-2.86 (m, 1H), 2.43 (t, J=7.8 Hz, 2H), 2.01 (dd, J=12.5, 3.4 Hz, 2H), 1.82 (d, J=12.5 Hz, 2H), 1.73-1.70 (m, 3H), 1.62-1.49 (m, 2H), 1.43-1.14 (m, 7H), 0.89 (t. J=6.7 Hz, 3H). $^{13}C$ NMR (101 MHz, $CDCl_3$) δ 154.71, 142.20, 116.95, 108.93, 77.36, 35.57, 35.39, 31.70, 30.80, 30.64, 27.53, 26.36, 22.69, 14.17. MS (ESI): 262 [M, 62%], 219 (70%), 206 (64%), 137 (100%).

Example 7. 2-[6-(1,5-Dimethylhex-4-en-1-yl)-3-methylcyclohex-2-en-1-yl]-5-pentylbenzene-1,3-diol

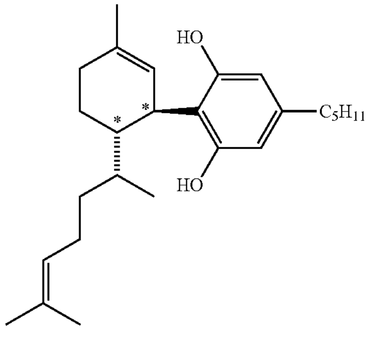

The 150 ml round-bottom Schlenk flask was equipped with a magnetic stir bar and a rubber septum. The flask was flushed with nitrogen and olivetol (2.00 g, 11.1 mmol), toluene (35 mL), and p-toluenesulfonic acid monohydrate (125 mg, 6 mol %) were added. Then flask was placed in a pre-heated (70° C.) oil bath and stirred for 15 min, after which commercial ginger oil with a 48-50% content of zingiberene (5.40 mL) was injected through the septum within 1 min. After 25 min the reaction was quenched by pouring into a mixture of saturated aq. $NaHCO_3$ (20 mL) and ice (10 g). The organic phase was separated and the aqueous phase was extracted with ethyl acetate (2×40 mL). The combined organic phase was washed with water and brine, dried over magnesium sulfate and the solvent was evaporated to give the crude product (6.00 g). A chromatography cartridge was charged with 100 g of silica gel and equilibrated with a mixture of dichloromethane (10%) and hexane (90%). The crude product was loaded on the column and eluted with 7 column volumes the solvent mixture. The method was then changed to gradient elution, and within the next 8 column volumes the DCM content was gradually increased to 40%. The fractions containing the product were combined and the solvent was evaporated to give 2-[6-(1, 5-dimethylhex-4-en-1-yl)-3-methylcyclohex-2-en-1-yl]-5-pentylbenzene-1,3-diol (1.80 g, 42%) as a viscous, pale yellow oil. $^{1}H$ NMR (400 MHZ, $CDCl_3$) δ 6.26-6.15 (br m, 2H), 6.01 (br s, 1H), 5.53 (s, 1H), 4.89 (t, −7.3 I Hz, 1H), 4.51 (br s, 1H), 3.82 (d, J=10.5 Hz, 1H), 2.45 (t, J=7.8 Hz, 2H), 2.12-2.08 (m, 2H), 1.82-1.72 (m, 7H, incl. 1.77 s, 6H), 1.61-1.55 (m, 5H, incl 1.57 s, 3H), 1.42-1.18 (m, 8H), 0.90-0.83 (m, 7H). $^{13}C$ NMR (101 MHz, $CDCl_3$) δ 154.18 (br), 142.90, 139.94, 130.99, 124.97, 124.67, 113.78, 109.94 (br), 107.34 (br), 41.39, 35.77, 35.51, 35.36, 32.50, 31.60, 31.57, 30.84, 30.71, 25.99, 25.60, 23.66, 22.56, 22.47, 17.56, 14.55, 14.03. MS (ESI): 384 [M, 15%], 277 (10%), 246 (21%), 231 (100%).

Example 8. 2-(6-Isopropyl-3-methylcyclohex-2-en-1-yl)-5-pentyl-1,3-phenylene diacetate (H2CBD Diacetate)

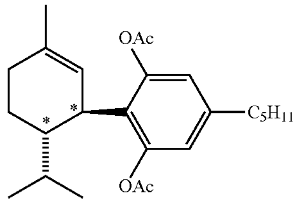

Acetic anhydride (1.24 mL, 1.34 g, 13.1 mmol) was added at room temperature to a stirred solution of H2CBD (1.60 g, 5.06 mmol) and pyridine (1.65 mL, 1.61 g, 20.0 mmol) in dichloromethane (100 mL). After 12 h the reaction mixture was poured into water (20 mL). The organic phase was separated, washed with saturated aq. $NaHCO_3$ and brine, dried over magnesium sulfate, then passed through a plug of silica gel (30 g) which was subsequently washed with additional DCM (50 mL). The solvent was evaporated to give H2CBD diacetate (1.82 g, 90%). $^{1}H$NMR (400 MHZ, $CDCl_3$) δ 6.73 (s, 2H), 5.14 (s, 1H), 3.43 (d, J=8.6 Hz, 1H), 2.70-2.45 (m, 2H), 2.21 (s, 6H), 2.10-2.00 (m, 2H), 1.90-1.77 (m, 2H), 1.66-1.59 (m, 4H, incl. 1.65 s, 3H), 1.49-1.41 (m, 1H), 1.37-1.25 (m, 5H), 0.89 (t, J=6.4 Hz, 3H), 0.83 (d, J=6.8 Hz, 3H), 0.76 (d, J=6.8 Hz, 3H). $^{13}C$ NMR (101 MHz, $CDCl_3$) δ 169.30, 150.06, 142.21. 133.33, 126.49, 125.11, 121.06 (br), 42.87, 37.57, 35.36, 31.69, 30.92, 30.52, 28.04, 23.55, 22.62, 22.49, 21.70, 21.11, 16.20, 14.15. MS (ESI): 400 [M, 56%], 357 (40%), 315 (38%), 273 (55%), 231 (100%).

Example 9. 2-(3-isopropyl-6-methyl-7-oxabicyclo [4.1.01hept-2-yl)-5-pentyl-13-phenylene diacetate (Epoxy-H2CBD Diacetate)

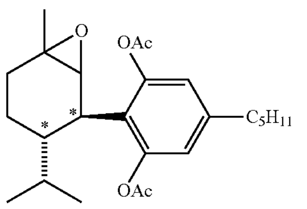

m-Chloroperbenzoic acid (75% w/w, 1.00 g, 4.35 mmol) was added to a stirred solution of H2CBD diacetate (1.35 g, 3.37 mmol) in dichloromethane (500 mL) in an ice bath. After 12 h the reaction was poured into water (20 mL), the organic phase was separated and was washed with aq. sodium bisulfite, aq. $NaHCO_3$, and brine, then dried over magnesium sulfate. The solvent was evaporated to give 2-(3-isopropyl-6-methyl-7-oxabicyclo[4.1.0]hept-2-yl)-5-pentyl-1,3-phenylene diacetate of 94% purity by GC (1.14 g, 84%) as yellowish oil. After purification with column chromatography (silica gel, pure DCM as an eluent), the more pure (97+ by GC) product was obtained as yellowish oil (470 mg, 35%). $^1$H NMR (400 MHZ, $CDCl_3$) δ ppm 6.76 (s, 1H), 6.78 (s, 1H), 3.09 (d, J=11.1 Hz, 1H), 2.88 (s, 1H), 2.56 (t, J=7.9 Hz, 2H), 2.30 (s, 6H), 2.11 (d, J=15.3 Hz, 1H), 1.72-1.56 (m, 3H), 1.38-1.15 (m, 11H, incl. 1.34 s, 3H), 0.90-0.86 (m, 3H), 0.72 (t, J=7.1 Hz, 6H). $^{13}$C NMR (101 MHz, $CDCl_3$) δ 168.99, 168.90, 149.78, 149.54, 142.86, 124.89, 121.09, 119.83, 64.07, 58.41, 43.12, 36.65, 35.37, 31.58, 31.08, 30.43, 27.86, 23.08, 22.52, 21.53, 21.42, 21.11, 17.98, 15.95, 14.06. MS (ESI): 426 [M, 4%], 374 (9%), 313 (48%), 271 (100%).

Example 10. 9-Isopropyl-6-methyl-3-pentyl-5a,6,7,8,9,9a-hexahydrodibenzo[b,d1furan-1,6-diol

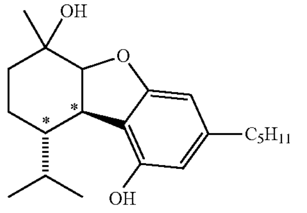

A 1M solution of KOH (1.81 mL, 1.81 mmol) was added to a solution of 2-(3-isopropyl-6-methyl-7-oxabicyclo [4.1.0]hept-2-yl)-5-pentyl-1,3-phenylene diacetate (470 mg, 1.13 mmol) in methanol (15 mL). After 30 min the reaction was diluted with water (70 mL) and extracted with ethyl acetate (3×20 mL). The extract was washed with aq. $NaHCO_3$ and brine, then dried over magnesium sulfate. The solvent was evaporated to give 9-isopropyl-6-methyl-3-pentyl-5a,6,7,8,9,9a-hexahydrodibenzo[b,d]furan-1,6-diol as a pale yellow oil (368 mg, 98%). $^1$H NMR (400 MHZ, $CDCl_3$) δ 6.31 (s, 1H), 6.17 (d, J=1.3 Hz, 1H), 5.00 (br s, 1H), 4.05 (dd, J=5.3, 1.6 Hz, 1H), 3.12 (dd, J=11.2, 5.3 Hz, 1H), 2.57-2.39 (m, 2H), 2.05-2.00 (m, 2H), 1.81-1.63 (m, 2H), 1.60-1.54 (s, 2H), 1.45 (s, 3H), 1.43-1.38 (m, 2H), 1.35-1.28 (m, 4H), 1.20-1.15 (m, 1H), 0.94 (d, J=6.9 Hz, 3H), 0.88 (t, J=6.8 Hz, 3H), 0.84 (d, J=6.9 Hz, 3H). $^{13}$C NMR (101 MHz, $CDCl_3$) δ 160.96, 151.91, 144.54, 117.65, 108.91, 103.47, 90.82, 69.93, 46.30, 40.58, 36.13, 35.10, 31.68, 31.09, 28.25, 27.38, 22.68, 21.92, 17.50, 15.76, 14.16.

Example 11. 5-(1,1-Dimethylpentyl)-2-(6-isopropyl-3-methylcyclohex-2-en-1-yl)benzene-1,3-diol

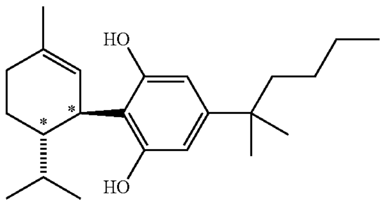 [SMILES: CCCCC(C)(C)c1cc(O)c([C@@H]2C=C(C)CC[C@H]2C(C)C)c(O)c1]

A 100 mL round-bottomed Schlenk flask was equipped with a magnetic stir bar and a rubber septum. The flask was flushed with nitrogen and 5-(1,1-dimethylpentyl)benzene-1,3-diol (1.58 g, 7.59 mmol), toluene (23 mL), and p-toluenesulfonic acid monohydrate (86 mg, 6 mol %) were added. The flask was placed in a pre-heated (70° C.) oil bath and stirred for 15 min, after which α-phellandrene (1.28 mL, 1.09 g, 7.96 mmol) was injected through the septum within 1 min. After 25 min the reaction was quenched by pouring into a mixture of saturated aq. $NaHCO_3$ (15 mL) and ice (5 g). The organic phase was separated and the aqueous phase was extracted with ethyl acetate (2×30 mL). The combined organic phase was washed with water and brine, dried over magnesium sulfate and the solvent was evaporated to give the crude product (2.61 g). The crude product was dissolved in hexane (25 mL) and loaded onto a plug (30 g) of silica gel. The plug was eluted with hexane (100 mL) followed by 250 mL of a 25:75 mixture of dichloromethane:hexane. The solvent was evaporated to give 5-(1,1-dimethylpentyl)-2-(6-isopropyl-3-methylcyclohex-2-en-1-yl)benzene-1,3-diol (2.21 g, 85%) as a viscous, pale yellow oil. $^1$H NMR (400 MHZ, $CDCl_3$) δ 6.40 (s, 1H), 6.25 (s, 1H), 4.62 (s, 1H), 3.33 (d, J=3.1 Hz, 1H), 1.89 (dd, J=13.2, 2.6 Hz, 1H), 1.85-1.82 (m, 1H), 1.75 (dd, J=13.6, 3.5 Hz, 1H), 1.61-1.56 (m, 2H), 1.54-1.48 (m, 4H), 1.36 (s, 3H), 1.32-1.27 (m, 1H), 1.24-1.19 (m, 8H, incl. 1.21 s, 6H), 1.10 (d, J=6.5 Hz, 3H), 1.07-1.03 (m, 2H), 0.96 (d, J=6.5 Hz, 3H), 0.83 (t, J=7.3 Hz, 3H). $^{13}$C NMR (101 MHz, $CDCl_3$) δ 157.27, 151.92, 149.87, 111.51, 105.81, 104.01, 74.63, 44.45, 44.42, 37.53, 35.14, 30.64, 29.52, 28.97, 28.95, 27.90, 27.09, 26.37, 23.54, 22.20, 21.26, 20.69, 14.25.

Example 12. 5-(1,1-Dimethylheptyl)-2-(6-isopropyl-3-methylcyclohex-2-en-1-yl)benzene-1,3-diol

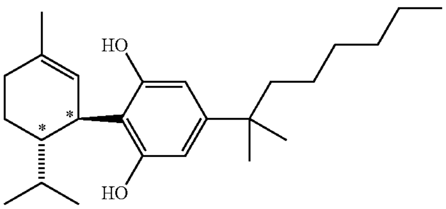 [SMILES: CCCCCCC(C)(C)c1cc(O)c([C@@H]2C=C(C)CC[C@H]2C(C)C)c(O)c1]

A 100 mL round-bottomed Schlenk flask was equipped with a magnetic stir bar and a rubber septum. The flask was flushed with nitrogen and 5-(1,1-dimethylheptyl)benzene-1,3-diol (1.50 g, 6.44 mmol), toluene (20 mL), and p-toluenesulfonic acid monohydrate (74 mg, 6 mol %) were added. The flask was placed in a pre-heated (70° C.) oil bath and stirred for 15 min, after which α-phellandrene (1.08 mL, 921 mg, 6.75 mmol) was injected through the septum within 1 min. After 25 min the reaction was quenched by pouring into a mixture of saturated aq. $NaHCO_3$ (10 mL) and ice (5 g). The organic phase was separated and the aqueous phase was extracted with ethyl acetate (2×20 mL). The combined organic phase was washed with water and brine, dried over magnesium sulfate and the solvent was evaporated to give the crude product (2.38 g). The crude product was dissolved in hexane (20 mL) and loaded onto a plug (30 g) of silica gel. The plug was eluted with hexane (100 mL) followed by 250 mL of a 25:75 mixture of dichloromethane:hexane. The solvent was evaporated to give 5-(1,1-dimethylheptyl)-2-(6-isopropyl-3-methylcyclohex-2-en-1-yl)benzene-1,3-diol (1.86 g, 78%) as a viscous, pale yellow oil. $^1H$ NMR (400 MHZ, $CDCl_3$) δ 6.40 (s, 1H), 6.25 (s, 1H), 4.48 (s, 1H), 3.32 (d, J=3.1 Hz, 1H), 1.89 (dd, J=13.2, 2.6 Hz, 1H), 1.85-1.79 (m, 1H), 1.77-1.69 (m, 1H), 1.61-1.55 (m, 2H), 1.53-1.47 (m, 4H), 1.35 (s, 3H), 1.30-1.26 (m, 1H), 1.24-1.16 (m, 12H, incl. 1.21 s, 6H), 1.11 (d, J=6.5 Hz, 3H), 1.08-1.04 (m, 2H), 0.95 (d, J=6.5 Hz, 3H), 0.85 (t, J=7.0 Hz, 3H). $^{13}C$ NMR (101 MHz, $CDCl_3$) δ 157.30, 151.90, 149.91, 111.47, 105.86, 104.00, 44.70, 44.46, 35.15, 31.94, 30.64, 30.18, 30.17, 29.53, 28.99, 28.95, 27.92, 26.38, 24.79, 22.84, 22.21, 21.28, 20.70, 14.25, 14.25. MS (ESI): 372 [M, 22%], 3163 (9%), 288 (100%).

Example 13. 2,4-Dihydroxy-3-(6-isopropyl-3-methylcyclohex-2-en-1-yl)-6-pentylbenzoic acid (H2CBDA)

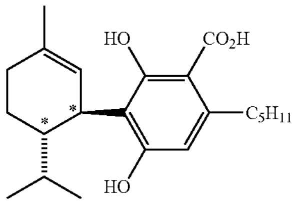

Magnesium metal (0.765 g, 31.6 mmol) was heated under reflux in absolute methanol (15 mL) for 1 h, at which point the metal had been fully consumed. The solvent was evaporated and the magnesium methoxide product was re-dissolved in dry DMF (10 mL). The mixture placed in an ice-bath and stirred, and solid carbon dioxide (1.4 g, 32 mmol) was introduced in a single portion. After 30 min a solution of H2CBD (1.00 g, 3.16 mmol) in DMF (2 mL) was added and the mixture was heated in an oil bath at 120° C. for 3 h. The reaction was quenched by pouring into a mixture of ice (20 g), water (50 mL) and conc. hydrochloric acid (3.8 mL). After stirring 10 min, the mixture was adjusted to pH 3 with 1 N hydrochloric acid and extracted with ethyl acetate (3×20 mL). The combined organic phase was washed with water and brine and dried over magnesium sulfate. The solvent was evaporated to give the crude product (1.10 g) which was purified by flash chromatography using 85:15 hexane:ethyl acetate to give 2,4-dihydroxy-3-(6-isopropyl-3-methylcyclohex-2-en-1-yl)-6-pentylbenzoic acid (175 mg, 39%) as a viscous yellow oil which solidified on standing, along with unreacted H2CBD (610 mg, 61%). $^1H$ NMR (600 MHZ, $CDCl_3$) δ 11.91 (s, 1H), 6.74 (s, 1H), 6.28 (s, 1H), 5.51 (s, 1H), 4.00 (d, J=9.8 Hz, 1H), 3.04-2.90 (m, 1H), 2.88-2.78 (m, 1H), 2.19-2.08 (m, 2H), 1.85-1.76 (m, 4H, incl. 1.78, s, 3H), 1.67-1.51 (m, 4H), 1.47-1.40 (m, 1H), 1.40-1.24 (m, 6H), 0.93-0.84 (m, 10H). $^{13}C$ NMR (101 MHz, $CDCl_3$) δ 176.10, 164.26, 161.30, 147.68, 140.67, 124.51, 114.89, 112.25, 102.59, 43.78, 36.57, 35.07, 32.04, 31.28, 30.54, 27.84, 23.69, 22.53, 22.02, 21.71, 16.56, 14.07.

Example 14. Antiseizure Study

Animals: Male, Wistar Han rats (70-110 g; Harlan, Bicester, UK) were housed on a 12 h light-dark cycle, with food and water available ad libitum. All experiments were conducted in accordance with the UK Animals (Scientific Procedures) Act, 1986 and ARRIVE guidelines for reporting experiments involving animals; 60 rats were used in total.

Drug administration: Animals were randomly divided into 5 groups of 12 animals per group and received either vehicle (ethanol, Cremophor EL and saline (0.9% w/v NaCl), 2:1:17), a positive control (cannabidiol; CBD; 200 mg $kg^{-1}$; Sigma-Aldrich, UK) or 8,9-dihydrocannabidiol (H2CBD; 50, 100 or 200 mg $kg^{-1}$) via i.p. injection 1 h prior to administration of the convulsant agent to achieve brain cannabinoid Tmax. The convulsant agent pentylenetetrazole (PTZ; 85 mg $kg^{-1}$ in 0.9% w/v NaCl) was administered i.p. 1 h after drug or vehicle treatment. Seizure activity was video recorded for 30 min and video records blinded before offline review and coding using a modified Racine scale (0, normal behaviour; 0.5, abnormal behaviour; 1, isolated myoclonic jerk; 2, atypical clonic seizure; 3, bilateral forelimb clonus; 3.5, bilateral forelimb clonus with body twist; 4, tonic-clonic seizure with suppressed tonic phase; 5, fully developed tonic-clonic seizure).

Assessment of bioanalytes: Chemicals and reagents. 4,4-Dichlorodiphenyltrichloroethane (DDT, CAS: 50-29-3) was used as the internal analytical standard (IS). HPLC grade n-hexane, acetonitrile, water and ascorbic acid were purchased from Sigma Aldrich (UK) and Fisher Scientific.

Analysis of plasma and brain samples: Stock standard solutions of CBD, H2CBD and DDT were prepared in acetonitrile (5 mg/ml and 1 mg/mL) and stored at −20° C. until use. These were further diluted in acetonitrile:water (62:38), to achieve calibration concentrations of 0.1, 0.2, 0.5, 1.5, 10 μg/mL. Plasma samples were prepared for HPLC using a previously validated method. Briefly, DDT (50 pg/mL) was added to 150 μL of rat plasma sample as internal standard and plasma proteins were precipitated by the addition of 600 μL of ice cold acetonitrile followed by water (600 μL), with 1 min vortexing between additions. n-Hexane (3 mL) was added to each tube and following a 5 min vortex, tubes were centrifuged at 1160×g for 15 min at 10° C. and the upper organic layer was carefully decanted by glass pipette and retained. The organic layer was evaporated to dryness under a stream of nitrogen at room temperature and reconstituted in 150 μL of the mixture of acetonitrile and water (62:38) prior to HPLC analysis.

For brain analysis, brains were weighed and 1.5× ice-cold solvent (90% acetonitrile; 10% water; 0.1% ascorbic acid) (w/v) was added followed by homogenization for 1 min. DDT (50 μg/ml) was added to each homogenized brain tissue as internal standard, samples were mixed and allowed to equilibrate overnight at −20° C. Samples were then centrifuged at 3500 rpm for 15 min and the top layer retained. Samples were dried by SpeedVac concentrator at room temperature (Savant SPD131DDA, ThermoFisher Scientific, UK) and reconstituted in 150 μL of the mixture of acetonitrile and water (62:38) for HPLC analysis.

HPLC analysis: An Agilent 1200 series HPLC (Hewlett-Packard, Palo Alto, CA, USA) equipped with a photodiode array detector was used for analysis. 30 μl of all samples were injected and separation was achieved using an ACE C18-PFP 150 mm×4.6 mm, 3 μm particle size column (Hichrom Ltd., Reading, UK), protected by an ACE C18-PFP 3 pm guard cartridge. The mobile phase was a mixture of acetonitrile and water in a ratio of 62:38 (v/v). The flow rate was set at 1 mL/min and column temperature was maintained at 55° C. The absorbance of all compounds of interest (CBD and DH-CBD) was monitored at 220 nm.

Statistics: Statistical procedures were performed using GraphPad Prism 7 (GraphPad Software, Inc., San Diego, CA, USA). A D'Agostino and Pearson normality test revealed that data describing maximum seizure severity and bioanalyte concentrations were not normally distributed. Therefore, assessment of differences within groups of these data types were assessed by a Kruskal-Wallis test with post-hoc Dunn's tests. Drug effects upon the percentage of animals exhibiting tonic-clonic seizures were assessed by a chi-squared test with post-hoc Fisher exact tests.

H2CBD has previously been the subject of a limited number of studies involving cannabinoid pharmacology. Consistent with CBD, H2CBD shows 1) an inhibitory effect on cytochrome P450, which can be measured by CO complex formation during hepatic microsomal metabolism of H2CBD, and 2) antioxidant activity quantified by inhibition of the production of reactive oxygen intermediates, nitric oxide, and tumor necrosis factor in murine macrophages. In contrast to CBD, H2CBD shows little if any evidence of sedative activity.

In the present study, 60 male, Wistar Han rats were randomly divided into 5 groups of 12 animals each and received either vehicle (ethanol, Cremophor EL, 0.9% w/v saline; 2:1:17), vehicle plus a positive control (CBD; 200 mg $kg^{-1}$), or vehicle plus H2CBD (50, 100, or 200 mg $kg^{-1}$) via intraperitoneal injection one hour prior to administration of the convulsant agent pentylenetetrazole (PTZ; 85 mg $kg^{-1}$ in 0.9% w/v saline).

Figure 2:
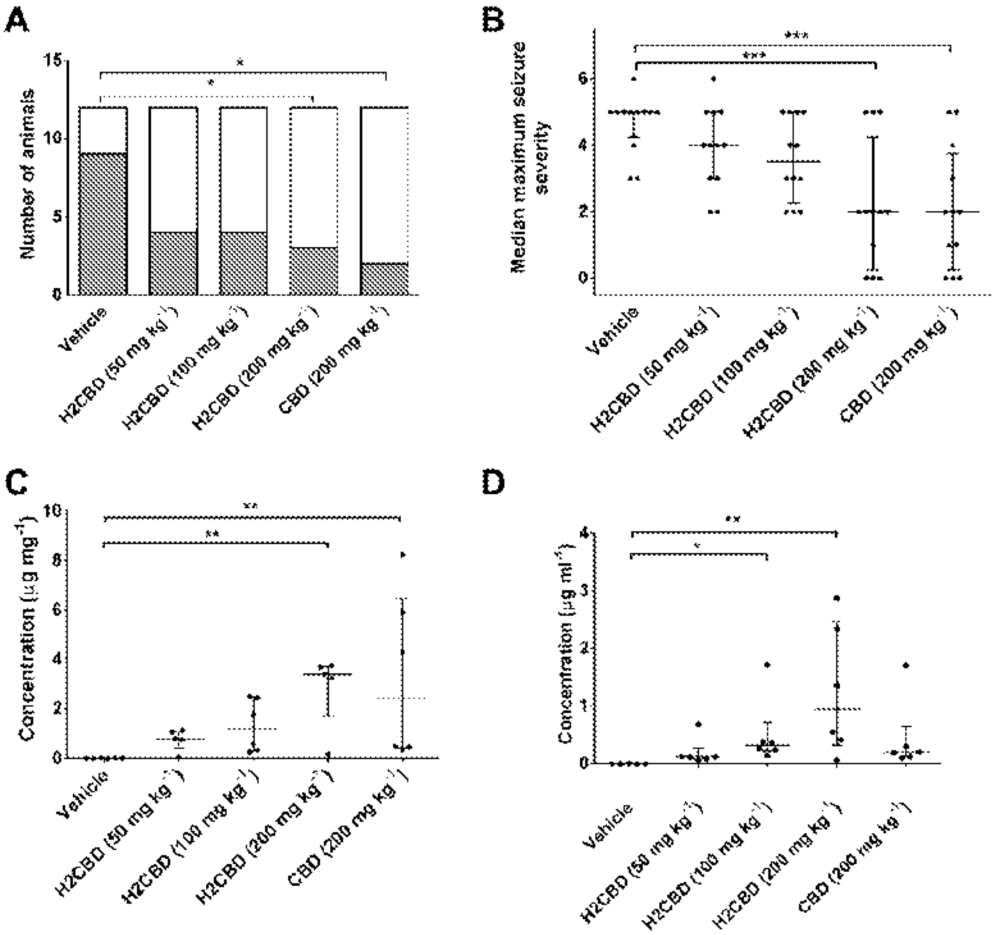
FIG. 2A-2D shows effect of H2CBD upon acute, PTZ-induced primary generalised seizures in rat. Effects of vehicle, H2CBD (50, 100 & 200 mg $kg^{-1}$), and CBD (200 mg $kg^{-1}$) treatments upon (FIG. 2A) the proportion of animals exhibiting tonic-clonic seizures (gray shaded area) and (FIG. 2B) median (middle bars), interquartile range (upper and lower bars) and individual (•) maximum seizure severity, following PTZ administration. *=$P<0.05$; *=$P<0.001$. Error bars in (FIG. 2B) show SEM. n=12 animals per group in each case.

An overall effect of treatment upon the percentage of animals that exhibited tonic-clonic seizures was found ($\chi^2$ (4)=10.48; P=0.033), where pairwise comparisons revealed that significantly fewer animals that received CBD (200 mg $kg^{-1}$) and H2CBD (200 mg $kg^{-1}$) exhibited tonic-clonic seizures than the vehicle treated group (P<0.05 in both cases) (FIG. 2). Furthermore, maximum seizure severity was also affected by treatment (H 18.96; P<0.001). where pairwise comparisons revealed that animals that received CBD (200 mg $kg^{-1}$) and H2CBD (200 mg $kg^{-1}$) exhibited significantly less severe seizures as coded by the Racine scale than the vehicle treated group (vehicle median: 5 (4.25-5 IQR), H2CBD 200 mg $kg^{-1}$:2 (0.25-4.25 IQR), CBD 200 mg $kg^{-1}$:2 (0.25-3.75 IQR), P<0.001 in both cases).

Analysis of blood and brain tissue obtained from rats in each treatment group post-mortem revealed an overall effect of dosing upon blood (H=17.00; P=0.0019) and brain tissue (H=15.76; P=0.0034) arising from detection of significant concentrations of H2CBD (100 mg/kg: P<0.05 (blood); 200 mg/kg: P<0.01 (blood); P<0.01 (brain)) and CBD (200 mg/kg: P<0.01 (brain)) when compared with the vehicle treated group (FIG. 2).

The results unequivocally demonstrate that H2CBD exhibits a dose-dependent anticonvulsant action in acute, PTZ-induced generalised seizures in rats, with a maximal protective effect comparable to a matching dose of the established anticonvulsant CBD. While these preliminary data provide a clear indication for the use of H2CBD as an anticonvulsant agent, further work will establish the inherent pharmacokinetic profile of H2CBD which, for the purposes of this preliminary study, was assumed to be identical to CBD, although indications from the bioanalyte results suggest differences in plasma and brain concentration at matching doses (200 mg $kg^{-1}$), despite a comparable anticonvulsant effect. This may suggest the magnitude of the anticonvulsant effect of H2CBD could be attenuated by suboptimal dosing intervals, preventing the effect from being assessed at maximal drug concentration.

The effect of H2CBD was then assessed on rodent behavior. Multiple studies have demonstrated the anxiolytic/sedative properties of CBD, and recent work has suggested a possible mechanism for this effect. It was previously found that when CBD is exposed to simulated gastric fluid, CBD exhibited nearly complete degradation mainly to $\Delta^8$- and $\Delta^9$-THCs within one hour, suggesting oral administration of CBD could expose patients to levels of THC that exceed the threshold for inducing narcosis. In the absence of behavioral studies on H2CBD in the dose range used in the present work, the activity of H2CBD was evaluated against vehicle in EPM and open field tests.

12 adult male Sprague Dawley rats were divided at random into two groups of 6 animals each and received either vehicle (Kolliphor RH-40, dmso, 0.9% w/v saline, 1:2:7) or vehicle plus H2CBD (200 mg $kg^{-1}$), administered by intraperitoneal injection. The vehicle differed in this case from the anti-seizure study to avoid the potentially confounding effect of alcohol. The number of animals was also limited to the lowest population necessary to establish an effect at the maximum dosage of drug. At 45 minutes post vehicle and drug injections, rats were placed in the center of the EPM and time spent on the open versus closed arms of the maze was recorded. After an interval of two weeks, the same 12 rats were again divided at random into two groups of 6 animals each and dosed as above. Spontaneous locomotor activity was measured 45 minutes after injection by placing the animals in the center of a 16"×16" arena. Free movement was allowed for 30 minutes and recorded using an automated activity monitoring system.

Figure 3:
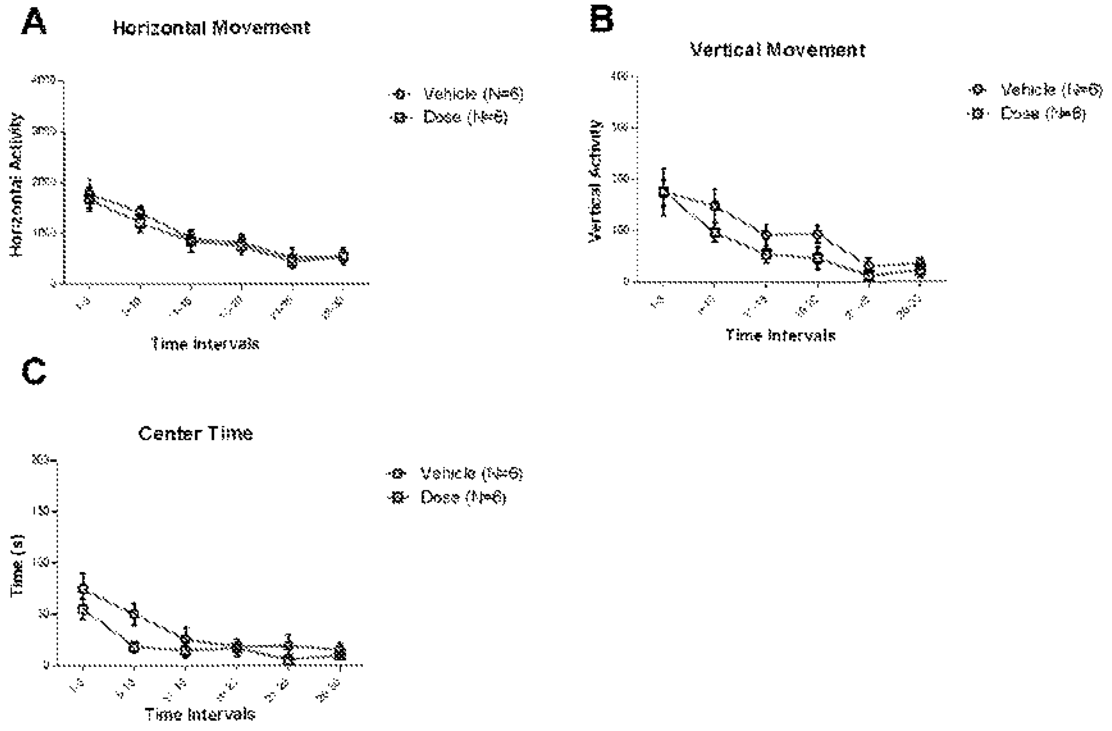
FIG. 3A-3C shows locomotor activity in the open field measured for 30 min starting 45 min after drug or vehicle injection. Horizontal plane movement (FIG. 3A), vertical plane movement (FIG. 3B), and time in the center of the open field arena (FIG. 3C) are shown for the drug and vehicle groups.
Figure 4:
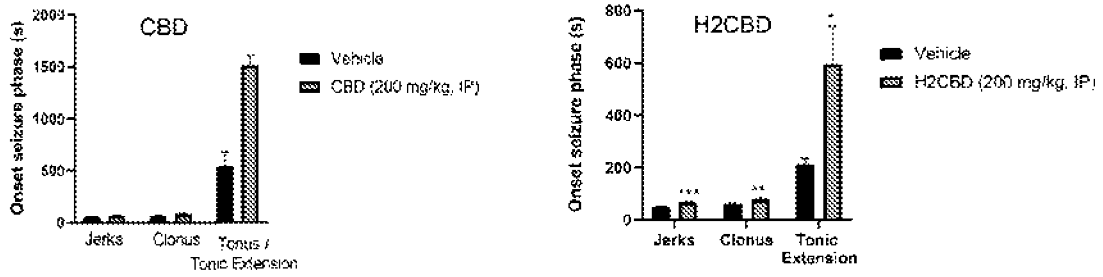
FIG. 4 shows comparison of positive control CBD (left) with H2CBD (right) in the prevention of PTZ-induced seizures in mice. Both drugs were dosed at 200 mg $kg^{-1}$ and PTZ was dosed at 85 mg $kg^{-1}$. Tonus was observed as wild running followed by no hind limb extension. Tonic extension was observed as wild running followed by extension of hind limbs. Clonus refers to involuntary, rhythmic muscular contractions and relaxations. Jerk refers to sudden, involuntary muscle contractions. * P=0.025,  P=0.004, * P=0.0002 compared to the vehicle group.

The EPM data were analyzed by variance. No statistically significant differences were found between drug and vehicle treated groups in percent time spent on the open arms (F 1,10=0.50, p=0.49). In the open field test, there were no statistically significant differences between drug and vehicle treated groups for horizontal distance traveled ($F_{1,10}$=0.005, P=0.95), vertical activity ($F_{1,10}$=1.52, p=0.25), or time in the arena center ($F_{1,10}$=2.55 p=0.14) (FIG. 3). Since H2CBD cannot be converted to THC by any mechanistically reasonable pathway, the above data are consistent with the hypothesis that CBD itself has no intrinsic anxiolytic or sedative activity, but that in vivo conversion to THC may be responsible for the effect. In any case, the data indicates that H2CBD produces no measurable behavioral effects at high dosage (200 mg $kg^{-1}$).

In conclusion, it has been demonstrated that prophylactic administration of H2CBD (200 mg $kg^{-1}$) to rats significantly reduces incidence of tonic-clonic seizures as well as maximum seizure severity as compared to vehicle treatment, without producing changes in behavior. The advantages of H2CBD over CBD as a potential antiepileptic drug are summarized as follows: 1) Being fully synthetic, H2CBD is not a controlled substance and thereby circumvents legal issues surrounding cannabis-based therapies. 2) The preparative approach to H2CBD is efficient, inexpensive, and scalable. Unlike CBD, which has to be isolated from a mixture of other extractives and may be contaminated with pesticides, synthetic H2CBD is easy to obtain in pure form. 3) H2CBD can be used as a medication at high dosages without narcotic side effects. 4) In contrast to CBD, there is no practical synthetic pathway from H2CBD to THC. 5) Preparation of H2CBD from readily available, non-cannabis based precursors eliminates the necessity to cultivate hemp and its attendant concerns. Thus, assuming the principal medical justification for pursuing cannabis-based therapies is their extraordinary anticonvulsant activity, and that all other indications (anxiety, chronic pain, nausea, anorexia, etc) can be effectively managed with non-controversial drugs, the oft-cited case for legalizing marijuana based on this therapeutic advantage may be called into question.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula Ie:

(Ie)

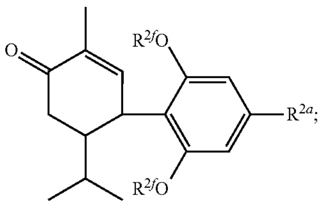

Formula If:

(If)

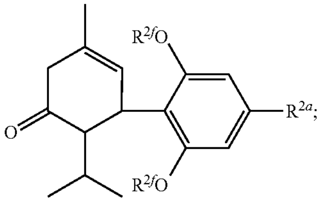

Formula Ik:

(Ik)

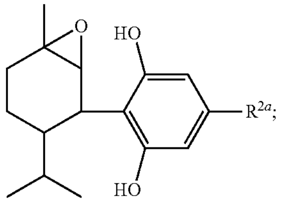

or

Formula IA-1e (IA-1e)

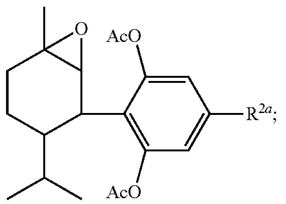

wherein $R^{2a}$ is $C_{4-15}$ alkyl, $C_{2-20}$ alkenyl or $C_{2-20}$ alkynyl; and $R^{2f}$ is hydrogen, $C_{1-20}$ alkyl, $C_{2-20}$ alkenyl or $C_{2-20}$ alkynyl.

2. A compound or a pharmaceutically acceptable salt of the structure:

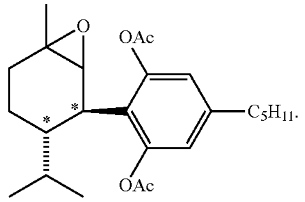

* * * * *